(12) United States Patent
Steinman et al.

(10) Patent No.: US 10,098,935 B2
(45) Date of Patent: Oct. 16, 2018

(54) AQUAPORIN TOLERIZING VACCINES AND METHODS OF USE THEREOF

(71) Applicant: The Board of Trustees of the Leland Stanford Junior University, Stanford, CA (US)

(72) Inventors: Lawrence Steinman, Stanford, CA (US); Peggy P. Ho, Cupertino, CA (US)

(73) Assignee: The Board of Trustees of the Leland Stanford Junior University, Stanford, CT (US)

( * ) Notice: Subject to any disclaimer, the term of this patent is extended or adjusted under 35 U.S.C. 154(b) by 0 days.

(21) Appl. No.: 15/134,931

(22) Filed: Apr. 21, 2016

(65) Prior Publication Data

US 2016/0317629 A1    Nov. 3, 2016

Related U.S. Application Data

(60) Provisional application No. 62/195,625, filed on Jul. 22, 2015, provisional application No. 62/155,947, filed on May 1, 2015.

(51) Int. Cl.
*A61K 39/00* (2006.01)
*A61K 48/00* (2006.01)

(52) U.S. Cl.
CPC ...... *A61K 39/0008* (2013.01); *A61K 2039/53* (2013.01); *A61K 2039/54* (2013.01); *A61K 2039/55566* (2013.01); *A61K 2039/577* (2013.01)

(58) Field of Classification Search
CPC . C12N 5/0636; A61K 39/0008; C07K 14/705
See application file for complete search history.

(56) References Cited

U.S. PATENT DOCUMENTS

| 7,544,669 | B2 | 6/2009 | Fontoura et al. | |
| 8,524,508 | B2 * | 9/2013 | Lennon | C07K 16/18 436/543 |
| 8,748,404 | B2 | 6/2014 | Steinman et al. | |

FOREIGN PATENT DOCUMENTS

| WO | 2003/045316 A2 | 6/2003 |
| WO | 2012/015903 A1 | 2/2012 |
| WO | WO 2015/075213 A1 * | 5/2015 |
| WO | WO 2016/037123 A * | 3/2016 |

OTHER PUBLICATIONS

Kalluri et al 2011, PLoS ONE 6: (e16083) pp. 1-11.*
Steinman et al 2010, J. Intern. Med. 267:441-451.*
Steinman, et al (2016) "Restoring immune tolerance in neuromyelitis optica: Part I", Neurology, Neuroimmunology & Neuroinflammation, 3(5), article e276, pp. 1-10.*
Boccaccio et al., "Non-coding plasmid DNA induces IFN-g in vivo and suppresses autoimmune encephalomyelitis", International Immunology, 1999, pp. 289-296, vol. 11, No. 2, The Japanese Society for Immunology, Tokyo, Japan.
Collongues et al., "Current and future treatment approaches for neuromyelitis optica", Ther Adv Neurol Disord, 2011, pp. 111-121, 4(2), SAGE Publications, Thousand Oaks, CA.
Denic et al., "The relevance of animal models in multiple sclerosis research", Pathophysiology, 2011, pp. 21-29, Elsevier, Amsterdam, Netherlands.
Feldmann et al., "Design of effective immunotherapy for human autoimmunity", Nature, Jun. 2, 2005, pp. 612-619, vol. 435, Nature Publishing Group, London, United Kingdom.
Ho et al., "Tolerizing DNA vaccines for autoimmune arthritis", Autoimmunity, Dec. 2006; pp. 675-682, 39(8), Informa Group PLC, London, United Kingdom.
Jones et al., "Review of Animal Models of Neuromyelitis Optica", Mult Scler Relat Disord, Oct. 2012, pp. 174-179, 1(4), Elsevier, Amsterdam, Netherlands.
Marrie et al., "The Incidence and Prevalence of Neuromyelitis Optica", International Journal of MS Care, 2013, pp. 113-118, he Consortium of Multiple Sclerosis Centers, Hackensack, NJ.
Wingerchuk et al., "Revised diagnostic criteria for neuromyelitis optica", Neurology, May 23, 2006, pp. 1485-1489, vol. 66 No. 10, American Academy of Neurology, Minneapolis, MN.
Papadopoulos et al., "Aquaporin 4 and neuromyelitis optica", Lancet Neurol, Jun. 11, 2012, pp. 1-19, 11(6), Elsevier, Amsterdam, Netherlands.
Life Technologies Corporation, "pVAX1 User Guide" Catalog No. V260-20, Mar. 2, 2012, Publication Part No. 25-0256 Life Technologies Corporation, Pleasanton, CA.
Solvason et al., "Improved Efficacy of a Tolerizing DNA Vaccine for Reversal of Hyperglycemia through Enhancement of Gene Expression and Localization to Intracellular Sites", The Journal of Immunology, 2008, pp. 8298-8307, The American Association of Immunologists, Inc., Bethesda, MD.

* cited by examiner

*Primary Examiner* — Robert M Kelly
(74) *Attorney, Agent, or Firm* — Pamela J. Sherwood; Bozicevic, Field & Francis LLP

(57) ABSTRACT

The instant disclosure provides aquaporin DNA tolerizing vaccines and methods of using such vaccines for treating individuals having neuromyelitis optica (NMO) and NMO spectrum disorders. Aspects of the methods include administering to the individual, in need thereof, an effective amount of an aquaporin DNA tolerizing vaccine to reduce one or more symptoms of NMO or an NMO spectrum disorder. Compositions and kits for practicing the methods of the disclosure are also provided.

7 Claims, 8 Drawing Sheets
(7 of 8 Drawing Sheet(s) Filed in Color)
Specification includes a Sequence Listing.

pBHT1-Murine AQP4 p21-40 construct

FIGURE 3

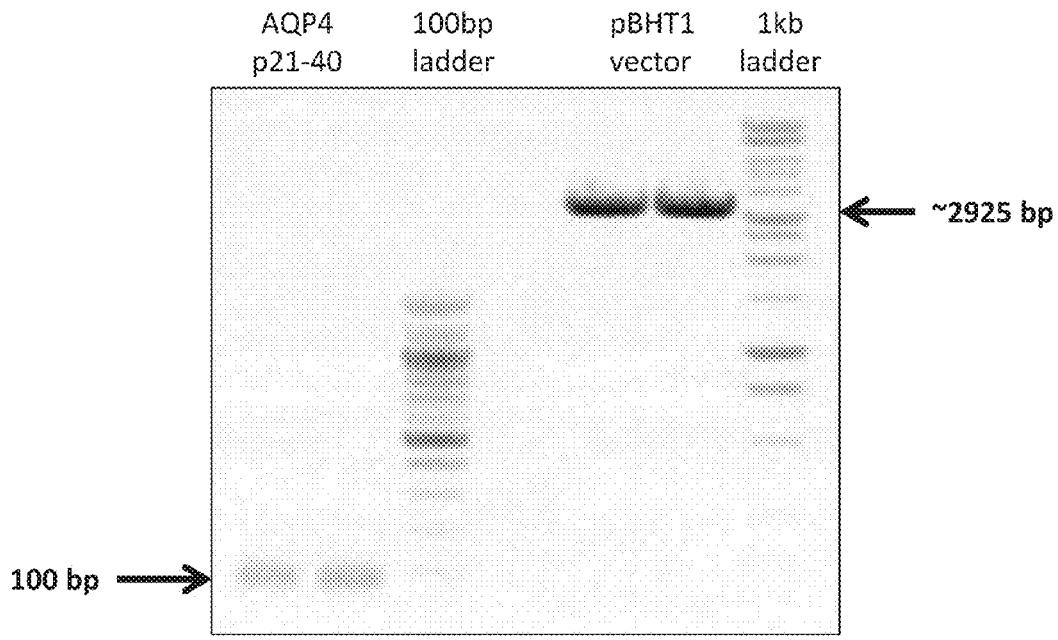

FIGURE 4

DNA sequencing & BLAST search confirm pBHT1-AQP4 p21-40 vector

>ref|NM_009700.2| U E G M Mus musculus aquaporin 4 (Aqp4), mRNA
Length=5082

GENE ID: 11829 Aqp4 | aquaporin 4 (Mus musculus) (Over 100 PubMed links)

Score = 115 bits (62), Expect = 1e-22
Identities = 69/72 (96%), Gaps = 2/72 (3%)
Strand=Plus/Plus

```
Query  41   GAGCATCATGGTGGCTTTCAAAGGAGTCTGGACTCAGGCTTTCTGAAGGCAGTCTCAGC  100
            ||||||||||||||||||||||||||||||||||||||||||||||||||||||||||
Sbjct  113  GAGCATCATGGTGGCTTTCAAAGGAGTCTGGACTCAGGCTTTCTGAAGGCAGTCTCAGC  170

Query  101  ATGAGAATCTG  112
            | || | |||||
Sbjct  173  A-GA-ATTCTG  182
```

NMO: DNA vaccination experiment #1 - treatment

AQUAPORIN TOLERIZING VACCINES AND METHODS OF USE THEREOF

CROSS-REFERENCE

This application claims the benefit of U.S. Provisional Patent Application No. 62/155,947, filed May 1, 2015 and U.S. Provisional Patent Application No. 62/195,625, filed Jul. 22, 2015, which applications are incorporated herein by reference in its entirety.

SEQUENCE LISTING PROVIDED AS A TEXT FILE

A Sequence Listing is provided herewith as a text file, "STAN-1197_ST25.txt" created on Apr. 20, 2016 and having a size of 14 KB. The contents of the text file are incorporated by reference herein in their entirety.

INTRODUCTION

Neuromyelitis optica (NMO) or Devic's disease is a severe, demyelinating disease of the central nervous system that preferentially affects the optic nerve and spinal cord. NMO and NMO spectrum disorder attacks are characterized mainly by uni- or bilateral inflammation of the optic nerve, optic neuritis, and acute, traverse myelitis. Most patients have relapsing attacks (separated by months or years with partial recovery) and most relapsing patients are female. A less common form of NMO results in a single attack lasting one to two months. In some rare instances, patients suffer other neurological disorders including, intractable vomiting, nausea, endocrine disorders, sleep disorders, confusion, and coma. Untreated or unrecognized, NMO can be fatal within 5 years of onset in nearly a third of patients. Many NMO patients may become legally blind in one or both eyes and may have significant partial paralysis. The etiology of NMO remains unknown.

NMO has an estimated prevalence of about 0.5 to 4.4 per 100,000 people and incidence per 100,000 people of about 0.05 to 0.4 worldwide. Diagnosis of NMO is typically clinical and generally based on the co-presence of primary symptomatic optic neuritis and myelitis with other supporting criteria, typically normal brain MRI (i.e., imaging that is not diagnostic of multiple sclerosis), MRI evidence of extended myelitis in the spinal cord and/or the presence of biomarker NMO-IgG antibody (i.e., anti-aquaporin-4 (AQP4) antibody).

Data from randomized clinical treatment studies of NMO remains limited, thus, treatment modalities for NMO are varied. Current palliative and preventative treatments include corticosteroids, plasma exchange, immunomodulatory therapy with purified immunoglobulins from healthy donors, interferon therapy and various conventional immunosuppressive therapies.

PUBLICATIONS

Collongues & de Seze (2011) *Ther Adv Neurol Disord.* 4(2): 111-121.
Marrie & Gryba (2013) *Int J MS Care.* 15(3): 113-118.
Wingerchuk et al. (2006) *Neurology.* 66(10):1485-9.

SUMMARY

Methods are provided for treating individuals having neuromyelitis optica (NMO) and NMO spectrum disorders. Aspects of the instant disclosure include aquaporin DNA tolerizing vaccines and methods of using such vaccines. Aspects of the subject methods further include administering to the individual, in need thereof, an effective amount of an aquaporin DNA tolerizing vaccine to at least reduce one or more symptoms of NMO or an NMO spectrum disorder and/or prevent the onset of one or more symptoms of NMO or an NMO spectrum disorder as described herein. Also provided are compositions and kits for practicing the methods of the disclosure.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 3 depicts confirmation by restriction enzyme digest of the successful cloning of the AQP4 p21-40 insert as described in FIG. 2.

FIG. 4 depicts confirmation by DNA sequencing and BLAST search of the successful cloning of the AQP4 p21-40 insert as described in FIG. 2 (SEQ ID NO:2).

DETAILED DESCRIPTION OF THE EMBODIMENTS

Figure 1:
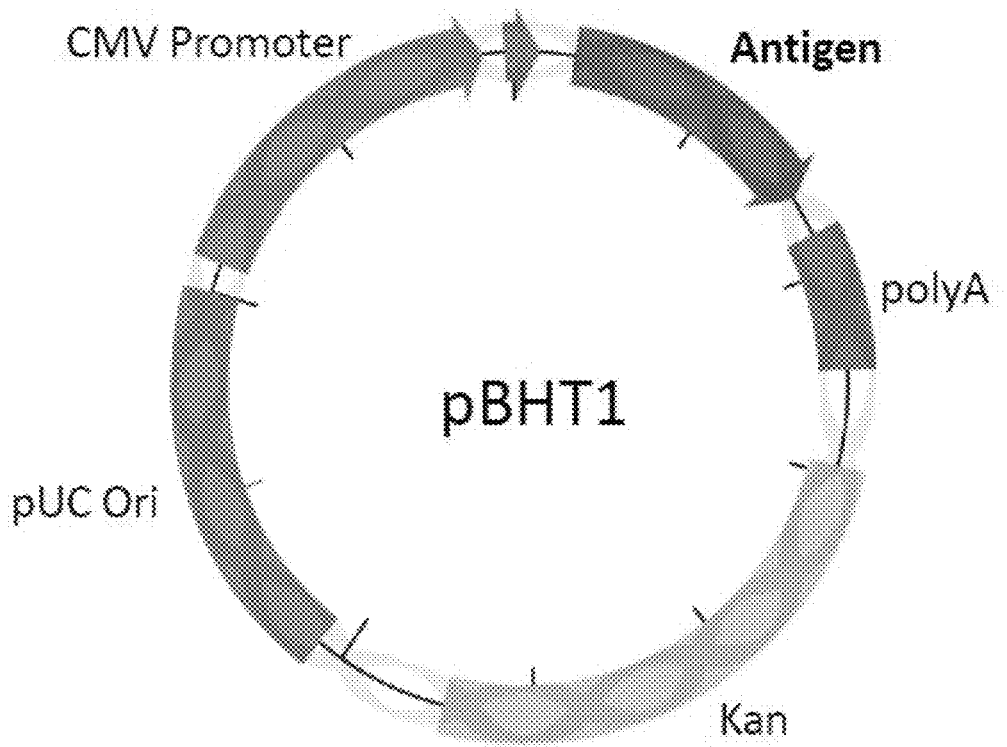
FIG. 1 depicts a schematic of the pBHT1 vector showing the relative positions of the antigen sequence, the polyadenylation signal, the Kanamycin resistance sequence, the pUC origin of replication and the CMV promoter.

The instant disclosure provides aquaporin DNA tolerizing vaccines and methods of using such vaccines for treating individuals having neuromyelitis optica (NMO) and NMO spectrum disorders. Aspects of the methods include administering to the individual, in need thereof, an effective amount of an aquaporin DNA tolerizing vaccine to reduce one or more symptoms of NMO or an NMO spectrum disorder. Compositions and kits for practicing the methods of the disclosure are also provided.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed

DEFINITIONS

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

A "vector" is capable of transferring nucleic acid sequences to target cells. For example, a vector may comprise a coding sequence capable of being expressed in a target cell. For the purposes of the present invention, "vector construct," "expression vector," and "gene transfer vector," generally refer to any nucleic acid construct capable of directing the expression of a gene of interest and which is useful in transferring the gene of interest into target cells. Thus, the term includes cloning and expression vehicles, as well as integrating vectors, however, in some instances a vector may be configured to prevent, eliminate or inhibit the integration of the vector into a host cell genome.

The term "plasmid" is encompassed within the term "vector" and refers to any genetic element that is capable of replication by comprising proper control and regulatory elements when present in a host cell. Plasmids may be designated by a lower case p followed by letters and/or numbers. Starting plasmids are commercially available, publicly available on an unrestricted basis, can be constructed from available plasmids in accord with published procedures, can be isolated from organisms harboring the plasmid (e.g., naturally occurring organisms or laboratory stocks (e.g., bacterial stocks, etc.), or synthesized, in whole or in part, on a standard or custom basis, e.g., as provided by commercial suppliers such as DNA2.0, Inc. (Menlo Park, Calif.)). In addition, where equivalent plasmids to those described are known in the art such plasmids will be readily apparent to the ordinarily skilled artisan and the nucleic acid sequences of such plasmids may be readily available.

Vectors are capable of transferring nucleic acid sequences to target cells and, in some instances, are used to manipulate nucleic acid sequence, e.g., recombine nucleic acid sequences (i.e. to make recombinant nucleic acid sequences). For purposes of this invention examples of vectors include, but are not limited to, plasmids, phage, transposons, cosmids, virus, and the like.

"Naked nucleic acid" as used herein refers to a nucleic acid molecule that is not encapsulated (such as, e.g., within a viral particle, bacterial cell, or liposome) and not complexed with a molecule that binds to the nucleic acid (such as, e.g., DEAE-dextran) nor otherwise conjugated to the nucleic acid (e.g., gold particles or polysaccharide-based supports).

An "expression cassette" comprises any nucleic acid construct capable of directing the expression of any RNA transcript including gene/coding sequence of interest as well as non-translated RNAs. Such cassettes can be constructed into a "vector," "vector construct," "expression vector," or "gene transfer vector," in order to transfer the expression cassette into target cells. Thus, the term includes cloning and expression vehicles, as well as viral vectors.

The terms "polypeptide" and "protein" are used interchangeably to refer to a polymer of amino acid residues linked by peptide bonds, and for the purposes of the instant disclosure, have a minimum length of at least 5 amino acids. Oligopeptides, oligomers multimers, and the like, typically refer to longer chains of amino acids and are also composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 5 amino acids are encompassed by the definition. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity relevant to the purposes of the described methods. These modifications can be deliberate, as through site-directed mutagenesis, or can be accidental, such as through mutations of hosts that produce the proteins, or errors due to PCR amplification or other recombinant DNA methods.

Modified polypeptides may also include, e.g., those polypeptides that have been modified to improve their use as a therapeutic. Such polypeptide modification may include any combination of N- and/or C-terminal truncation (e.g., to achieve the minimal active sequence (MAS)), deletion of one or more consecutive amino acid(s) to achieve the MAS, combinatorial deletion with two or more positions omitted independently to achieve the MAS, structure simplification (e.g., following alanine or D amino acid scanning to identify non-active sites), cleave site elimination, cyclization between side chains, cyclization between terminal ends, cyclization between the backbone, cyclization between a terminal end and a side chain, cyclization between a terminal end and the backbone, cyclization between a side chain and the backbone, cyclization through disulfide bonding, modification to reduce polypeptide flexibility (e.g., through peptide bridging, e.g., lanthionine bridging, dicarba bridging, hydrazine bridging, lactam bridging), modification to reduce hydrogen bonding, modification to increase membrane permeability (e.g., by modifying the overall or regional (e.g., surface) charge of a polypeptide), unnatural amino acid (e.g., a D-amino acid) substitution, N-methyl-α-amino acid substitution, n-amino acid substitution, amide bond replacement, terminal end blocking (e.g., through N-acylation, N-pyroglutamate, C-amidation, etc.), addition of carbohydrate chains, N-terminal esterification, pegylation, and the like. Polypeptide modifications have been described, e.g., by Vlieghe et al. (2010) *Drug Discovery Today.* 15:(1/2) 40-56, the disclosure of which is incorporated herein by reference. The ordinary skilled artisan will readily understand where a polypeptide modification may be encoded (e.g., an amino acid substitution, amino acid addition, amino acid truncation, etc.) in a nucleic acid. The ordinary skilled artisan will also readily understand that where a polypeptide modification is initially synthetically produced (e.g., through enzymatic truncation of a polypeptide) such modification may, in some instances, also be achieved by modifying a nucleic acid that encodes the polypeptide.

The term "gene" refers to a particular unit of heredity present at a particular locus within the genetic component of an organism. A gene may be a nucleic acid sequence, e.g., a DNA or RNA sequence, present in a nucleic acid genome, a DNA or RNA genome, of an organism and, in some instances, may be present on a chromosome. Typically a gene will be a DNA sequence that encodes for an mRNA that encodes a protein. A gene may be comprised of a single exon and no introns or multiple exons and one or more introns. One of two or more identical or alternative forms of a gene present at a particular locus is referred to as an "allele" and, for example, a diploid organism will typically have two alleles of a particular gene. New alleles of a particular gene may be generated either naturally or artificially through natural or induced mutation and propagated through breeding or cloning.

The terms "specific binding," "specifically binds," and the like, refer to non-covalent or covalent preferential binding to a molecule relative to other molecules or moieties in a solution or reaction mixture (e.g., an antibody specifically binds to a particular polypeptide (e.g., antigen) or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Life Technologies. Inc., Sigma-Aldrich, and ClonTech.

Aquaporin Polypeptides and Nucleic Acids

Aspects of the disclosure include aquaporin polypeptides and nucleic acids encoding for aquaporin polypeptides for use in treating neuromyelitis optica. By "aquaporin polypeptide" is meant a polypeptide having homology with the product of one or more aquaporin genes encoding an aquaporin protein. Aquaporin proteins form water specific channels that provide plasma membranes with permeability to water and serve to regulate cellular, tissue, organ and organismal water balance by mediating water flow along osmotic gradients and/or functioning as osmoreceptors. DNA tolerizing vectors, described in more detail below, may include one or more nucleic acid sequences encoding for one or more aquaporin polypeptides or portion(s) thereof.

Aquaporin polypeptides may be recombinantly or synthetically produced and may vary in their homology with naturally occurring aquaporin polypeptides. As such, an aquaporin polypeptide of the instant disclosure may share 100% or less sequence identity with a naturally occurring aquaporin polypeptide. An aquaporin polypeptide having less than 100% sequence identity with a naturally occurring aquaporin polypeptide may be a modified polypeptide, e.g., recombinantly modified, such that one or more amino acid residues of a naturally occurring aquaporin polypeptide sequence have been modified such that the recombinant aquaporin polypeptide is a non-naturally occurring aquaporin polypeptide.

In some instances, a recombinant aquaporin polypeptide may be encoded from a recombinant aquaporin nucleic acid. Such recombinant aquaporin polypeptides may contain one or more amino acid residue mutations relative to a naturally occurring aquaporin polypeptide. By "mutations" is meant any amino acid reside substitution, deletion or insertion in the primary amino acid sequence relative to a starting aquaporin polypeptide, e.g., a naturally occurring aquaporin polypeptide or other reference aquaporin polypeptide sequence. Amino acid mutations may be generated through synthetic means, e.g., through mutation of a naturally occurring or reference nucleic acid sequence encoding an aquaporin polypeptide. In some instances, a recombinant aquaporin nucleic acid excludes one or more non-coding sequences included in a naturally occurring aquaporin gene or genetic locus. For example, in some instances, a recombinant aquaporin nucleic acid may be an aquaporin cDNA that excludes one or more introns of an aquaporin gene or genetic locus. The number of excluded non-coding sequences in an aquaporin cDNA may vary depending on, e.g., the overall length of the cDNA, the particular aquaporin gene from which the cDNA may be derived, the length of the particular aquaporin from which the cDNA may be derived, the particular isoform from which the cDNA may be derived, the particular aquaporin allele or mutant allele from which the cDNA may be derived, etc., and may range from 1 to 3 or more, including 1 or more, 2 or more, 3 or more. In some instances, an aquaporin cDNA may comprise the entire coding region of the aquaporin gene and exclude all non-coding sequences, e.g., all introns and untranslated regions, of the reference gene locus and/or transcript.

In some instances, an aquaporin polypeptide or aquaporin nucleic acid may be derived, in part or in whole, from a mammalian aquaporin gene. Mammalian aquaporin genes include placentalia aquaporins, monotremata aquaporins and marsupialia aquaporins. Placentalia aquaporins include those of primates, rodents, even-toes ungulates, carnivores, bats, odd-toed ungulates, insectivores, rabbits and hares, *cingulata*, macroscelidea, tenrecidae, scandentia, dermoptera, proboscidea, tubulidentata, chrysochloridae, and sirenia. Primate aquaporins include but are not limited to those of baboons (e.g., *Papio papio, Papio Anubis, Papio cynocephalus, Papio hamadryas, Papio ursinus* and the like), macaques (e.g., *Macaca fascicularis*, *Macaca nemestrina*, *Macaca mulatta*, and the like), green monkeys (e.g., *Chlorocebus* genus), mangabey (e.g., *Cercocebus agilis*, *Cercocebus galeritus*, *Cercocebus torquatus*. *Cercocebus atys*, *Cercocebus lunulatus*, and the like), patas monkeys (e.g., *Erythrocebus patas*), squirrel monkeys (e.g., *Saimiri sciureus*), species of the family Hominidae (e.g., chimpanzees, gorillas, orangutans, and humans). Rodent aquaporins include but are not limited to those of mouse, rat, squirrel, gopher, vole, hamster, gerbil, guinea pig and the like.

In some instances, an aquaporin protein, e.g., as encoded by an aquaporin gene, may be described in terms of sequence similarity and/or sequence identity in relationship to a described amino acid sequence. As such, an aquaporin polypeptide may share up to 100% sequence identity with a particular amino acid sequence, e.g., one or more of the aquaporin amino acid sequences described herein. In some instances, an aquaporin polypeptide may share less than 100% sequence identity to a particular amino acid sequence, e.g., one or more of the aquaporin amino acid sequences described herein, including but not limited to, e.g., at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71% or at least 70% sequence identity with an aquaporin amino acid sequence described herein. In some instances, an aquaporin polypeptide may share no less than 60% sequence identity to one or more of the aquaporin sequences described herein.

In some instances, an aquaporin protein, e.g., as encoded by an aquaporin gene, may share 100% sequence identity with an aquaporin 4 (AQP4) polypeptide including but not limited to a mammalian AQP4 polypeptide, a rodent AQP4 polypeptide, a human AQP4 polypeptide, a mouse AQP4 polypeptide, and the like. In some instances, an aquaporin polypeptide may share less than 100% sequence identity to a AQP4 polypeptide, e.g., one or more of the AQP4 polypeptide amino acid sequences described herein, including but not limited to, e.g., at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71% or at least 70% sequence identity with an AQP4 amino acid sequence described herein. In some instances, an aquaporin polypeptide may share no less than 60% sequence identity to one or more of the AQP4 sequences described herein.

In some instances, an aquaporin polypeptide may, in whole or in part, share 100% sequence identity or less than 100% sequence identity (including but not limited to, e.g., 99%, 95%, 90%, 85%, 80%, etc.) with one or more proteins of UniProt ID Nos: P47863, Q5I4F9, Q923J4, H0Y2J1, U5L133, U5L0U2, U5L1A8, U5L0F3, U5L1A7, U5L0K2, U5L0T9, A0A096NGN8, Q866S4, Q6XVT6, U5L134, H2NW35, H0V364, A0A091E3Y2, O77750, F71QC1. H2QED7, U5L0K6, G3SXM7. G1SVZ6, P55087, F1DSG4, F6TNF8, G3R4L3. G7PWJ7, P55088, L8HYR7, H0WNR2, G3WQD1, G3WQD2, F6SPF1, U5L0F5, M3XDP6, G1M6L3, Q53H97, G1R432, U5L1A9, D2GUV5, 13MKS2, F7I6W3, Q9H3V7, G5BJS5, F7FSF9, A8V978, L5LSC4, F1PEB5, M3Y5D3, U6CQ82, L5K2V7, L9KGP3, G3HDY9, Q8K4M1. In some instances, an aquaporin polypeptide may share at least 90% (including, e.g., 95%, 96%, 97%, 98% 99%, etc.) amino acid sequence similarity over at least 80% (including, e.g., 85%, 90%, 95%, 96%, 97%, 98% 99%, etc.) of its length with one or more of of UniProt ID Nos: P47863, Q5I4F9, Q923J4, H0Y2J1, U5L133, U5L0U2, U5L1A8, U5L0F3, U5L1A7, U5L0K2, U5L0T9, A0A096NGN8, Q866S4, Q6XVT6, U5L134, H2NW35, H0V364, A0A091E3Y2, O77750, F71IQC1, H2QED7, U5L0K6, G3SXM7, G1SVZ6, P55087, F1DSG4, F6TNF8. G3R4L3. G7PWJ7, P55088, L8HYR7, H0WNR2, G3WQD1, G3WQD2, F6SPF1, U5L0F5, M3XDP6, G1M6L3, Q53H97, G1R432, U5L1A9, D2GUV5, 13MKS2, F7I6W3, Q9H3V7, G5BJS5, F7FSF9, A8V978, L5LSC4, F1PEB5, M3Y5D3, U6CQ82, L5K2V7, L9KGP3, G3HDY9, Q8K4M1.

In some embodiments of the invention, the aquaporin of interest is human aquaporin, including without limitation human aquaporin 4. The sequences of human aquaporins are publicly available, e.g. the reference sequence of aquaporin-4 isoform b GenBank accession number NP_004019.1; and the reference sequence of human aquaporin-4 isoform a GenBank accession number NP_001641.1.

In some instances, an aquaporin protein, e.g., as encoded by an aquaporin gene, may share 100% sequence identity or less (including but not limited to, e.g., at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71% or at least 70%) with a human aquaporin sequence, including but not limited to, e.g., human AQP4 (UniProtID: P55087) the amino acid sequence of which is:

(SEQ ID NO: 3)
MSDRPTARRWGKCGPLCTRENIMVAFKGVWTQAFWKAVTAEFLAMLI

FVLLSLGSTINWGGTEKPLPVDMVLISLCFGLSIATMVQCFGHISGG

HINPAVTVAMVCTRKISIAKSVFYIAAQCLGAIIGAGILYLVTPPSV

VGGLGVTMVHGNLTAGHGLLVELIITFQLVFTIFASCDSKRTDVTGS

IALAIGFSVAIGHLFAINYTGASMNPARSFGPAVIMGNWENHWIYWV

GPIIGAVLAGGLYEYVFCPDVEFKRRFKEAFSKAAQQTKGSYMEVED

NRSQVETDDLILKPGVVHVIDVDRGEEKKGKDQSGEVLSSV.

In some instances, an aquaporin protein, e.g., as encoded by an aquaporin gene, may share 100% sequence identity or less (including but not limited to, e.g., at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71% or at least 70%) with a mouse aquaporin sequence, including but not limited to, e.g., mouse AQP4 (UniProtID: P55088) the amino acid sequence of which is:

(SEQ ID NO: 4)
MSDGAAARRWGKCGHSCSRESIMVAFKGVWTQAFWKAVSAEFLATLI

FVLLGVGSTINWGGSENPLPVDMVLISLCFGLSIATMVQCFGHISGG

-continued

```
HINPAVTVAMVCTRKISIAKSVFYIIAQCLGAIIGAGILYLVTPPSV

VGGLGVTTVHGNLTAGHGLLVELIITFQLVFTIFASCDSKRTDVTGS

IALAIGFSVAIGHLFAINYTGASMNPARSFGPAVIMGNWANHWIYWV

GPIMGAVLAGALYEYVFCPDVELKRRLKEAFSKAAQQTKGSYMEVED

NRSQVETEDLILKPGVVHVIDIDRGEEKKGKDSSGEVLSSV.
```

In some instances, an AQP4 polypeptide or a nucleic acid encoding an AQP4 polypeptide may include or exclude all or a portion of a domain of the APQ4 protein. Domains of APQ4 include but are not limited to topological, transmembrane, and/or functional domains. Such domains include but are not limited to, e.g., Cytoplasmic Domain from amino acids 1 to 36 of P55087, Helical Domain from amino acids 37 to 57 of P55087, Extracellular Domain from amino acids 58 to 64 of P55087, Helical Domain from amino acids 65 to 85 of P55087, Cytoplasmic Domain from amino acids 86 to 115 of P55087, Helical Domain from amino acids 116 to 136 of P55087, Extracellular Domain from amino acids 137 to 155 of P55087, Helical Domain from amino acids 156 to 176 of P55087, Cytoplasmic Domain from amino acids 177 to 184 of P55087, Helical Domain from amino acids 185 to 205 of P55087, Extracellular Domain from amino acids 206 to 231 of P55087, Helical Domain from amino acids 232 to 252 of P55087, Cytoplasmic Domain from amino acids 253 to 323 of P55087. In some instances, an AQP4 polypeptide or a nucleic acid encoding an AQP4 polypeptide may include or exclude one or more APQ4 motifs, including but not limited to one or more (Asn-Pro-Ala) (i.e., NPA) motifs.

In some instances, an AQP4 polypeptide or a nucleic acid encoding an AQP4 polypeptide may include or exclude one or more modification sites of the APQ4 protein. Modification sites may include but are not limited to, e.g., phosphorylation sites, glycosylation sites. Such sites may include but are not limited to the following phosphoserine sites relative to the sequence of P55087: residue 111, residue 180, residue 285 and residue 321. Such sites include but are not limited to the following glycosylation sites relative to the sequence of P55087: residue 153 and residue 206. In some instances, an AQP4 polypeptide may include or exclude one or more post-translational modifications.

In some instances, an aquaporin polypeptide, e.g., as encoded from a nucleic acid of the subject disclosure, may include a portion of a full length aquaporin amino acid sequence, e.g., an aquaporin amino acid sequence disclosed herein. The length of such portions of aquaporin amino acid sequence may vary and may range, e.g., from 5 to 322 amino acids in length, including, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321 or 322 residues in length.

In some instances, such polypeptide portions of an aquaporin may include specific amino acid residues relative to the human AQP4 sequence (UniProt ID P55087) where the first amino acid of the polypeptide portion may range from residues 1-318 of P55087, including but not limited to, e.g., residue 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317 and 318.

In some instances, such polypeptide portions of an aquaporin may include specific amino acid residues relative to the human AQP4 sequence (UniProt ID P55087) where the last amino acid of the polypeptide portion may range from residues 5-323 of P55087, including but not limited to, e.g., residue 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, and 323.

In some instances, a polypeptide portion of an aquaporin may include amino acid residues 61-80 of the human AQP4 sequence (UniProt ID P55087).

In some instances, modification of an AQP4 polypeptide, including e.g., selection of amino acid mutations, amino acid deletions, and/or amino acid insertion sites, may be performed based on the three-dimensional structure of the AQP4 polypeptide. For example, in some instances, a modified AQP4 polypeptide and/or a nucleic acid encoding a modified AQP4 polypeptide may be based on rational design of the modified AQP4 polypeptide three-dimensional structure. Rational design of modified APQ4 polypeptides may be achieved through use of one or more three-dimensional APQ4 protein structures including but not limited to, e.g., RCSP Protein Data Bank (PDB) structure 3GD8 (see Ho et al., (2009) *Proc. Natl. Acad. Sci. USA* 106: 7437-7442, the disclosure of which is incorporated herein by reference in its entirety).

In some instances, an aquaporin nucleic acid, e.g., as included in a DNA tolerizing vaccine, may encode for an aquaporin polypeptide described herein, e.g., a mammalian AQP4 polypeptide, a human AQP4 polypeptide, a mouse AQP4 polypeptide. In some instances, an aquaporin nucleic acid may share 100% sequence identity over its entire length with all or a portion of an nucleic acid encoding for an aquaporin polypeptide described herein, e.g., a mammalian AQP4 polypeptide, a human AQP4 polypeptide, a mouse AQP4 polypeptide, etc.

In some instances, an aquaporin nucleic acid, e.g., as included in a DNA tolerizing vaccine, may be derived from human AQP4 nucleotide sequence. Human AQP4 nucleotide sequences include but are not limited to, e.g., those DNA sequences included in human genome locations chr18:24,432,008-24,442,575 and chr18:24,436,175-24,442,526. In some instances, an aquaporin nucleic acid may include, in part or in whole, or be derived from one or more sequences having the following Accession Numbers: U34846, U34845, D63412, U63622, U63623, AC018371, BC022286, RefSeq NM_001650.4, RefSeq NM_004028.3. In some instances, an aquaporin nucleic acid may include, in part or in whole, or be derived from CCDS11889.1 having the sequence:

```
                                        (SEQ ID NO: 5)
ATGAGTGACAGACCCACAGCAAGGCGGTGGGGTAAGTGTGGACCTTT

GTGTACCAGAGAGAACATCATGGTGGCTTTCAAAGGGGTCTGGACTC

AAGCTTTCTGGAAAGCAGTCACAGCGGAATTTCTGGCCATGCTTATT

TTTGTTCTCCTCAGCCTGGGATCCACCATCAACTGGGGTGGAACAGA

AAAGCCTTTACCGGTCGACATGGTTCTCATCTCCCTTTGCTTTGGAC

TCAGCATTGCAACCATGGTGCAGTGCTTTGGCCATATCAGCGGTGGC

CACATCAACCCTGCAGTGACTGTGGCCATGGTGTGCACCAGGAAGAT

CAGCATCGCCAAGTCTGTCTTCTACATCGCAGCCCAGTGCCTGGGGG

CCATCATTGGAGCAGGAATCCTCTATCTGGTCACACCTCCCAGTGTG

GTGGGAGGCCTGGGAGTCACCATGGTTCATGGAAATCTTACCGCTGG

TCATGGTCTCCTGGTTGAGTTGATAATCACATTTCAATTGGTGTTTA

CTATCTTTGCCAGCTGTGATTCCAAACGGACTGATGTCACTGGCTCA

ATAGCTTTAGCAATTGGATTTTCTGTTGCAATTGGACATTTATTTGC
```

AATCAATTATACTGGTGCCAGCATGAATCCCGCCCGATCCTTTGGAC

CTGCAGTTATCATGGGAAATTGGGAAAACCATTGGATATATTGGGTT

GGGCCCATCATAGGAGCTGTCCTCGCTGGTGGCCTTTATGAGTATGT

CTTCTGTCCAGATGTTGAATTCAAACGTCGTTTTAAAGAAGCCTTCA

GCAAAGCTGCCCAGCAAACAAAAGGAAGCTACATGGAGGTGGAGGAC

AACAGGAGTCAGGTAGAGACGGATGACCTGATTCTAAAACCTGGAGT

GGTGCATGTGATTGACGTTGACCGGGGAGAGGAGAAGAAGGGGAAAG

ACCAATCTGGAGAGGTATTGTCTTCAGTATGA.

In some instances, an aquaporin nucleic acid, e.g., as included in a DNA tolerizing vaccine, may be derived from mouse AQP4 nucleotide sequence. In some instances, an aquaporin nucleic acid may include, in part or in whole, or be derived from one or more sequences having the following Accession Numbers: U48398, U48397, U33012, U48400, U48399. U88623. AF469168, AF469169, AF219992, CT010362, BC024526, RefSeq NM_009700.2, RefSeq XM_006525540.1. In some instances, an aquaporin nucleic acid may include, in part or in whole, or be derived from CCDS29073.1 having the sequence:

```
                                        (SEQ ID NO: 6)
ATGAGTGACAGAGCTGCGGCAAGGCGGTGGGGTAAGTGTGGACATTC

CTGCAGTAGAGAGAGCATCATGGTGGCTTTCAAAGGAGTCTGGACTC

AGGCTTTCTGGAAGGCAGTCTCAGCAGAATTTCTGGCCACGCTTATC

TTTGTTTTGCTCGGTGTGGGATCCACCATAAACTGGGGTGGCTCAGA

AAACCCCTTACCTGTGGACATGGTCCTCATCTCCCTTTGCTTTGGAC

TCAGCATTGCTACCATGGTGCAGTGCTTTGGCCACATCAGTGGTGGC

CACATCAATCCCGCTGTGACTGTAGCCATGGTGTGCACACGAAAGAT

CAGCATCGCTAAGTCCGTCTTCTACATCATTGCACAGTGCCTGGGGG

CCATCATTGGAGCCGGCATCCTCTACCTGGTCACACCTCCCAGTGTG

GTTGGAGGATTGGGAGTCACCACGGTTCATGGAAACCTCACCGCTGG

CCATGGGCTCCTGGTGGAGTTAATAATCACTTTCCAGTTGGTGTTCA

CTATTTTTGCCAGCTGTGATTCCAAACGAACTGATGTTACTGGTTCA

ATAGCTTTAGCAATTGGATTTTCCGTTGCAATTGGACATTTGTTTGC

AATCAATTATACTGGAGCCAGCATGAATCCAGCTCGATCTTTTGGAC

CCGCAGTTATCATGGGAAACTGGGCAAACCACTGGATATATTGGGTT

GGACCAATCATGGGCGCTGTGCTGGCAGGTGCCCTTTATGAGTATGT

CTTCTGTCCTGATGTGGAGCTCAAACGTCGCCTTAAGGAAGCCTTCA

GCAAAGCCGCGCAGCAGACAAAAGGGAGCTACATGGAGGTGGAGGAC

AACCGGAGCCAAGTGGAGACGGAAGACTTGATCCTGAAGCCCGGAGT

GGTGCATGTGATTGACATTGACCGTGGAGAAGAGAAGAAGGGGAAAG

ACTCTTCGGGAGAGGTATTGTCTTCCGTATGA.
```

In some instances, a nucleic acid as described herein may be appended with one or more additional nucleic acids or one or more additional nucleotides. Additional nucleic acid may be appended to the described nucleic acids for a variety of purposes including but not limited to, e.g., cloning purposes (e.g., to facilitate homologous recombination, to facilitate ligation, etc.). As such, in some instances a nucleic acid as described herein may be appended with one or more additional nucleic acids to attach one or more nucleic acid spacers, one or more homologous sequences (e.g., a sequence homologous with a vector into which the subject nucleic acid may be cloned), one or more restriction enzyme recognition sites, and the like. Additional sequences appended to a subject nucleic acid may be added through any convenient method including but not limited to, e.g., ligation-based methods, PCR-based methods, de novo polynucleotide synthesis, etc.

DNA Tolerizing Vaccines

Aspects of the disclosure include DNA tolerizing vaccines comprising nucleic acid encoding for an aquaporin polypeptide. In some instances, an aquaporin polypeptide may be referred herein to as an antigen. Methods are provided, described in more detail below, for treating a subject having an adverse immune response to an aquaporin autoantigen. Accordingly, as used herein, the term "DNA tolerizing vaccine" may refer to a composition containing a nucleic acid containing one or more aquaporin nucleic acid sequences and encoding for one or more aquaporin polypeptides. In some instances, an encoded aquaporin polypeptide of a DNA tolerizing vaccine may be essentially the same as an aquaporin autoantigen. In some instances, an encoded aquaporin polypeptide of a DNA tolerizing vaccine may be different from an aquaporin autoantigen. Encompassed differences between an encoded aquaporin polypeptide of a DNA tolerizing vaccine and an aquaporin autoantigen include but are not limited to those polypeptide modifications described herein.

The components of an aquaporin DNA tolerizing vaccine will vary and will include, at a minimum, a vector that contains a nucleic acid sequence encoding an aquaporin polypeptide and the necessary components for expression of the aquaporin polypeptide from the vector. Nucleic acid sequence encoding for any aquaporin polypeptide, including those described herein, may find use in a DNA tolerizing vaccine.

In some instances, a DNA tolerizing vaccine includes a minigene that includes nucleic acid encoding for one or more aquaporin polypeptides. As used herein the term "minigene" refers to a minimal gene fragment that excludes one or more components of a native gene locus but includes the necessary elements for expression of the gene product or some portion of the gene product or a synthetic construct. In some instances, an aquaporin minigene may exclude at least one aquaporin intron, or portion thereof, including but not limited to 1 or more introns, 2 or more intron, or all the introns of the native aquaporin genetic locus. In some instances, an aquaporin minigene may include at least one aquaporin intron, or portion thereof, including but not limited to 1 or more introns, 2 or more intron, or all the introns of the native aquaporin genetic locus. In some instances, an aquaporin minigene may exclude at least one aquaporin exon, or portion thereof, including but not limited to 1 or more exons, 2 or more exons, 3 exons or all but a portion of one exon of the native aquaporin genetic locus. In some instances, an aquaporin minigene may include at least one aquaporin exon, or portion thereof, including but not limited to 1 or more exons, 2 or more exons, 3 exons or all the exons of the native aquaporin genetic locus.

In some instances, a minigene may include nucleic acid encoding for one antigenic epitope of an aquaporin gene. In some instances, a minigene may include two or more antigenic epitopes of an aquaporin gene, e.g., arranged in series and joined with or without one or more optional linkers. An antigenic epitope may consist of an exon or one or more portions thereof or portions of two or more exons. In some instances, multiple antigenic epitopes from the same exon and/or from multiple different exons are arranged in series and contained within a minigene. Methods of generating such strings of antigenic epitopes include but are not limited to, e.g., those described in Whitton et al. *J Virol.* 1993 January: 67(1): 348-352, the disclosure of which is incorporated herein by reference in its entirety.

A minigene will also include at least some regulatory sequence that controls or enhances the expression of the minigene transcript. In some instances, a minigene regulatory sequence will include a promoter. Promoters useful in an aquaporin minigene will vary and selection of such a minigene promoter will depend on various factors including the desired expression level of the minigene transcript, the desired control of minigene expression, the desired size of the overall minigene, the intended use of the minigene, including the subject to which the minigene may be delivered. Such minigene promoters may include but are not limited to a native aquaporin promoter, a native non-aquaporin (i.e., a promoter native to organism from which the aquaporin sequence was derived but not associated with the native aquaporin locus), a heterologous promoter (i.e., a promoter derived from an organism other than the organism from which the aquaporin sequence was derived (e.g., a non-human promoter, a non-mammalian promoter, etc.)), a minimal promoter, a minipromter, a constitutive promoter, a tissue specific promoter, an inducible promoter, a synthetic promoter and the like.

In some instances, a DNA tolerizing vaccine will include a vector backbone, e.g., a plasmid polynucleotide backbone. Vector backbones useful in a DNA tolerizing vaccine will vary and may be selected based on a number of factors. For example, in some instances, a vector backbone may be selected based on the absence or minimal presence of nucleotide sequence that is homologous with one or more desired host organisms of the DNA tolerizing vaccine (i.e., an organism that will ultimately receive the DNA tolerizing vaccine) in order to prevent or minimize the likelihood of homologous recombination between the vector and the host organism genome. The amount of homologous sequence between the vector backbone and the host organism may vary and, in some instances, the vector backbone may not contain any sequence homologous to the host organism that is longer than 200 nucleotides, including but not limited to, e.g., longer than 150 nucleotides, longer than 100 nucleotides, longer than 90 nucleotides, longer than 80 nucleotides, longer than 70 nucleotides, longer than 60 nucleotides, longer than 50 nucleotides, longer than 40 nucleotides, longer than 30 nucleotides or longer than 25 nucleotides. In some instances, the vector may have further features that prevent integration into a host genome, e.g., the vector may be a closed-circular plasmid.

A vector of a DNA tolerizing vaccine may include one or more vector specific elements. By "vector specific elements" is meant elements that are used in making, constructing, propagating, maintaining and/or assaying the vector before, during or after its construction and/or before its use in a DNA tolerizing vaccine. Such vector specific elements include but are not limited to, e.g., vector elements necessary for the propagation, cloning and selection of the vector during its use and may include but are not limited to, e.g., an origin of replication, a multiple cloning site, a prokaryotic promoter, a phage promoter, a selectable marker (e.g., an antibiotic resistance gene, an encoded enzymatic protein, an encoded fluorescent or chromogenic protein, etc.), and the like. Any convenient vector specific elements may find use, as appropriate, in the vectors as described herein.

In some instances, a vector backbone or one or more vector specific elements of a DNA tolerizing vaccine is configured to reduce the number of immunostimulatory motifs present in the vector. For example, a nucleic acid vector may be modified where a non-CpG dinucleotide is substituted for one or more CpG dinucleotides of the formula 5'-purine-pyrimidine-C-G-pyrimidine-pyrimidine-3' or 5'-purine-purine-C-G-pyrimidine-pyrimidine-3', thereby producing a vector in which immunostimulatory activity is reduced. Such vectors are useful, for example, in methods for administering immune modulatory nucleic acids and/or for administering a DNA tolerizing vaccine encoding one or more aquaporin polypeptides. For example, the cytosine of the CpG dinucleotide can be substituted with guanine, thereby yielding a region having a GpG motif of the formula 5'-purine-pyrimidine-G-G-pyrimidine-pyrimidine-3' or 5'-purine-purine-G-G-pyrimidine-pyrimidine-3'. The cytosine can also be substituted with any other non-cytosine nucleotide. The substitution can be accomplished, for example, using site-directed mutagenesis. Typically, the substituted CpG motifs are those CpGs that are not located in one or more regulatory regions of the vector (e.g., promoter regions) and/or vector specific element, as described herein. In addition, where the CpG is located within a coding region of an expression vector (e.g., the coding region of a vector specific element, such as a selectable marker), the non-cytosine substitution is typically selected to yield a silent mutation or a codon corresponding to a conservative substitution of the encoded amino acid.

For example, in certain embodiments, a modified pVAX1 vector is utilized in which one or more CpG dinucleotides of the formula 5'-purine-pyrimidine-C-G-pyrimidine-pyrimidine-3' is mutated by substituting the cytosine of the CpG dinucleotide with a non-cytosine nucleotide. The pVAX1 vector is known in the art and is commercially available from Life Technologies, Inc. (Grand Island, N.Y.). In one exemplary embodiment, the modified pVAX1 vector has the following cytosine to non-cytosine substitutions within a CpG motif: cytosine to guanine at nucleotides 784, 1161, 1218, and 1966; cytosine to adenine at nucleotides 1264, 1337, 1829, 1874, 1940, and 1997; and cytosine to thymine at nucleotides 1963 and 1987; with additional cytosine to guanine mutations at nucleotides 1831, 1876, 1942, and 1999 where the nucleotide number designations as set forth above are according to the numbering system for pVAX1 provided by Life Technologies, Inc. (Grand Island, N.Y.). In some instances, a modified pVAX1 vector is pBHT1 (SEQ ID NO:7).

In some instances, vectors, including vector specific elements, include or exclude certain immune modulatory sequences, e.g., exclude immunostimulatory sequences and/or include immunoinhibitory sequences, or have increased numbers of immunoinhibitory sequences and/or decreased numbers of immunostimulatory sequences. The use of immune modulatory sequences, including but not limited to, e.g.: GTGGTT, ATGGTT, GCGGTT, ACGGTT, GTGGCT, ATGGCT, GCGGCT, ACGGCT, GTGGTC, ATGGTC, GCGGTC, ACGGTC, GTGCTT, ATGCTT, GCGCTT, ACGCTT, GTGCCT, ATGCCT, GCGCCT, ACGCCT, GTGCTC, ATGCTC, GCGCTC, ACGCTC, GGGGTT, AGGGTT, GAGGTT, AAGGTT, GGGGCT, AGGGCT, GAGGCT, AAGGCT, GGGGTC, AGGGTC, GAGGTC, AAGGTC, GGGCTT, AGGCTT, GAGCTT, AAGCTT, GGGCCT, AGGCCT, GAGCCT, AAGCCT, GGGCTC, AGGCTC, GAGCTC and AAGCTC; and the generation and use of vectors containing reduced numbers of immunostimulatory sequences and increased numbers of immunoinhibitory sequences have been described, e.g., in U.S. Pat. No. 7,811,813, the disclosure of which is incorporated herein by reference in its entirety.

In some instances, the vector backbone (i.e., the nucleotide sequence of the vector excluding any regulatory elements, replication sequences and/or coding sequences), e.g., the resulting vector backbone after modification to remove immunostimulatory CpG motifs as described herein, contains 4 or fewer immunostimulatory CpG motifs, including but not limited to, e.g., 3 or fewer immunostimulatory CpG motifs, 2 or fewer immunostimulatory CpG motifs, 1 or fewer immunostimulatory CpG motifs. In some instances, a vector backbone as described herein of a DNA tolerizing vaccine may be modified to contain no immunostimulatory CpG motifs.

In some instances, the vector (i.e., the nucleotide sequence of the vector excluding only any inserted aquaporin coding sequence), e.g., the resulting vector after modification to remove immunostimulatory CpG motifs as described herein, contains 30 or fewer immunostimulatory CpG motifs, including but not limited to, e.g., 29 or fewer, 28 or fewer, 27 or fewer, 26 or fewer, 25 or fewer, 24 or fewer, 23 or fewer, 22 or fewer, 21 or fewer, 20 or fewer, 19 or fewer, 18 or fewer immunostimulatory CpG motifs.

A vector of a DNA tolerizing vaccine, whether or not configured to contain a minigene, will further include one or more regulatory elements. Such regulatory elements will vary and may include but are not limited to, e.g., a promoter, an enhancer, an intron, a polyadenylation signal, an initiation sequence (e.g., a Kozak sequence), and the like. Promoters useful in the expression of an aquaporin polynucleotide include but are not limited to, e.g., a native aquaporin promoter, a native non-aquaporin promoter (i.e., a promoter native to organism from which the aquaporin sequence was derived but not associated with the native aquaporin locus), a heterologous promoter (i.e., a promoter derived from an organism other than the organism from which the aquaporin sequence was derived (e.g., a non-human promoter, a non-mammalian promoter, etc.)), a minimal promoter, a minipromter, a constitutive promoter, a tissue specific promoter, an inducible promoter, a synthetic promoter and the like.

Promoters may be operably linked to an aquaporin polypeptide encoding nucleic acid to control production of encoded transcript either in vitro or in vivo. Such promoters may be constitutively active or controllable through the introduction of a stimulus, e.g., an environmental stimulus (e.g., change in temperature, pH, light exposure, and the like), a chemical or biological stimulus (e.g., a small molecule, a chemical, a polypeptide that binds to the promoter, and the like). In some instances, a vector of a DNA tolerizing vaccine may include a cytomegalovirus promoter.

A DNA tolerizing vaccine regulatory element may also include more or more enhancer elements. Enhancers may be operably linked to an aquaporin polypeptide encoding nucleic acid to control production of encoded transcript either in vitro or in vivo. Such enhancers may be constitutively active or controllable through the introduction of a stimulus, e.g., an environmental stimulus (e.g., change in temperature, pH, light exposure, and the like), a chemical or biological stimulus (e.g., a small molecule, a chemical, a polypeptide that binds to the enhancer, and the like). In some instances, a vector of a DNA tolerizing vaccine may include a cytomegalovirus enhancer.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable inducible promoters, including reversible inducible promoters are known in the art. Such inducible promoters may be isolated and derived from many organisms, e.g., eukaryotes and prokaryotes. Modification of inducible promoters derived from a first organism for use in a second organism, e.g., a first prokaryote and a second a eukaryote, a first eukaryote and a second a prokaryote, etc., is well known in the art. Such inducible promoters, and systems based on such inducible promoters but also comprising additional control proteins, include, but are not limited to, e.g., tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), temperature regulated promoters (e.g., heat shock inducible promoters (e.g., HSP-70, HSP-90, etc.), synthetic inducible promoters, and the like.

Transcriptional control elements, e.g., promoters, enhancers, etc., may be bound to an aquaporin polypeptide encoding nucleic acid singly or in arrays containing multiple transcriptional control elements, e.g., about 2, about 3, about 4, about 5, or more than 5 transcriptional control elements. In certain embodiments, transcriptional control elements are operably linked, directly or indirectly to the 5' end of an aquaporin polypeptide encoding nucleic acid with or without intervening "spacer" nucleic acid(s). Transcriptional control elements, methods of making and/or arranging and/or modifying transcription control elements (e.g., in expression cassettes) useful in the nucleic acids described herein may, in some instances, include those described in Liu et al., *Gene Therapy* (2004) 11:52-60; Zheng & Baum, *Methods Mol Biol.* 2008, 434:205-19; Papadakis et al., *Curr Gene Ther.* 2004, 4(1):89-113; the disclosures of which are incorporated herein by reference in their entirety.

A DNA tolerizing vaccine regulatory element may also include more or more introns wherein inclusion of the intron in the vector and/or minigene enhances the expression of the encoded aquaporin polypeptide of the DNA tolerizing vector. Such introns may be aquaporin gene introns (i.e., introns or portions thereof derived from a native aquaporin genetic locus) or may be native non-aquaporin introns (i.e., introns derived from the intended host genome but from a non-aquaporin locus) or may be heterologous introns (i.e., introns derived from a genome or organism other than the intended host genome or host organism). For example, in some instances, a DNA tolerizing vaccine may include an intron, or fragment thereof, from a cytomegalovirus including but not limited to the first intron of the cytomegalovirus or a minimal intron, including a minimal first intron, of the cytomegalovirus and/or those introns described in Quilici et al. *Biotechnol Lett.* 2013, 35(1):21-7 and Xu et al. *Gene.* 2001, 272(1-2):149-56; the disclosures of which are incorporated herein by reference in their entirety.

In some instances, a DNA tolerizing vaccine includes an appropriate diluent, e.g., a suitable solution or liquid for dissolving a vector as described herein. Such diluents may vary and may depend upon, e.g., the concentration of vector to be suspended, the pharmaceutical formulation, the DNA tolerizing vaccine, the mode of delivery of the DNA tolerizing vaccine, the method of storage of the DNA tolerizing vaccine, and the like. In some instances, a suitable solution or liquid may include but is not limited to, e.g., aqueous solutions, water (e.g., nuclease-free water, water for injection (WFI), etc.), saline, phosphate buffered saline (PBS), tris buffer saline (TBS), tris-EDTA (TE) buffer, combinations thereof, and the like. Pharmaceutical formulations of DNA tolerizing vaccines are discussed in more detail below.

Methods and Compositions

Aspects of the disclosure include methods and compositions for repressing an immune response to an aquaporin autoantigen in a subject. Because such methods can be used to treat a subject, such methods can also be referred to as methods of treating an individual. Aspects of the subject methods generally involve the administration of a therapeutically effective amount of a nucleic acid and/or DNA tolerizing vaccine, as described herein, to a subject in need thereof.

A "therapeutically effective amount" or "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of DNA tolerizing vaccine (e.g., APQ4 DNA tolerizing vaccine, and the like) and/or compositions (e.g., DNA tolerizing vaccine compositions) is an amount that is sufficient, when administered to (e.g., injected into, delivered intravenously, etc.) the individual, to palliate, ameliorate, stabilize, reverse, prevent, slow or delay the progression of the disease state (e.g., autoimmune disease, NMO spectrum disorder, NMO, etc.) by, for example, reducing the subject's immune activity, reducing the subject's immune response, reducing the subject's immune response to an aquaporin, reducing the subject's immune response to APQ4, reducing the subject's immune response to self-APQ4. In some instances, an effective amount reduces one or more symptoms of NMO and/or an NMO spectrum disorder (including but not limited to, e.g., vision impairment, vision loss, eye pain, eye strain, muscle weakness (e.g., in the arms and/or legs), numbness (e.g., in the arms and/or legs), partial paralysis (e.g., of the arms and/or legs), incontinence (e.g., urinary incontinence, fecal incontinence, etc.), intractable vomiting, intractable hiccups, nausea, endocrine disorders, sleep disorders, confusion, coma, etc.).

In some instances, a therapeutically effective dose, whether delivered in a single administration or multiple administrations, of a DNA tolerizing vaccine may remain effective for an extended period of time, e.g., by nature of the extended transient expression of the encoded polypeptide. The extended time period during which an administered therapeutically effective dose of a DNA tolerizing vaccine may remain effective will vary and may range from days to weeks including but not limited to, e.g., 2-3 days, 3-4 days, 4-5 days, 5-6 days, 6-7 days, 2-5 days, 3-6 days, 4-7 days, 1 week to 2 weeks, 2 weeks to 3 weeks, 3 weeks to 4 weeks, 1 week to 3 weeks, 2 weeks to 4 weeks, 1 week to 4 weeks, etc.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with NMO or an NMO spectrum disorder, e.g. those having NMO or an NMO spectrum disorder) as well as those in which prevention is desired (e.g., those with increased susceptibility to NMO or an NMO spectrum disorder; those with relapsing NMO; those suspected of having NMO or an NMO spectrum disorder; those having one or more risk factors for NMO or an NMO spectrum disorder or an NMO relapse, etc.).

A therapeutic treatment is one in which the subject is inflicted prior to administration and a prophylactic treatment is one in which the subject is not inflicted prior to administration. With respect to relapsing conditions, a prophylactic treatment may include a treatment administered to a subject with a diagnosed condition in a remitting state, e.g., to prevent a relapse of the condition or to prevent the reoccurrence of one or more symptoms of the condition. In some embodiments, the subject has an increased likelihood of becoming inflicted or is suspected of having an increased likelihood of becoming inflicted (e.g., relative to a standard, e.g., relative to the average individual, e.g., a subject may have a genetic predisposition to autoimmune disease and/or a family history indicating increased risk of NMO spectrum disorders and/or autoimmune disease), in which case the treatment can be a prophylactic treatment.

In some embodiments, the individual to be treated is an individual with NMO or an NMO spectrum disorder. As used herein "NMO" includes any form of NMO spectrum disorder, including relapsing NMO, acute NMO; unilateral NMO, bilateral NMO, and the like. In some cases, the individual has recently undergone treatment for NMO (e.g., corticosteroid therapy, immunomodulatory therapy, immunosuppressive therapy, etc.) and may therefore be at risk for recurrence and/or relapse. Those subjects in NMO remission may, in some instances, be treated according to the methods described herein, e.g., to prevent or delay relapse. In some instances, an NMO spectrum disorder suitable to be treated by the subject methods, compositions, and kits as described herein is a NMO diagnosed, at least in part, as based on the presence of NMO-IgG antibody in a sample from the subject.

The terms "individual", "subject", "recipient", "host", and "patient", are used interchangeably herein and refer to any mammalian subject for whom treatment or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human. In some instances, a subject may also be a research subject, including but not limited to, e.g., a human research subject (e.g., a clinical trial participant), a preclinical research subject (e.g., a mammalian research subject, a laboratory animal, etc.), an animal model (e.g., a rodent animal model, a mouse model, a rat model, etc.).

Animal models as used herein include but are not limited to animal models of multiple sclerosis (MS), animal models of MS related disorders, animal models of NMO, animal models of NMO spectrum disorders which may include but are not limited to, e.g., those described in Jones et al. (2012) *Mult Scler Relat Disord.* 1(4):174-179 and Denic et al. (2010) *Pathophysiology* 18: 21-29; the disclosures of which are incorporated herein by reference in their entirety. In some instances, a method of treatment and/or a DNA tolerizing vaccine and/or nucleic acid, as described herein, may be evaluated, tested, or developed through the use of one or more animal models. In such instances, a treated animal model or group thereof may be compared to one or more controls, including positive controls and/or negative controls, and/or control groups.

In some instances, a nucleic acid and/or DNA tolerizing vaccine, as described herein may be co-administered with one or more agents of one or more additional therapies. For example, a nucleic acid and/or DNA tolerizing vaccine may be co-administered with one or more conventional NMO therapies, e.g., steroid therapy, anti-inflammatory therapy, immunomodulatory therapy, immunosuppressive therapy, etc. In some instances, two or more nucleic acids and/or DNA tolerizing vaccines, as described herein may be administered in combination, e.g., as part of a nucleic acid and/or DNA tolerizing vaccine "cocktail".

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

Whether administered alone or as part of a combination therapy, any convenient and appropriate method of delivery of the nucleic acids and/or DNA tolerizing vaccines described herein may be utilized. Nucleic acid constructs can be delivered with cationic lipids (Goddard, et al, *Gene Therapy,* 4:1231-1236, 1997; Gorman, et al, *Gene Therapy* 4:983-992, 1997; Chadwick, et al, *Gene Therapy* 4:937-942, 1997; Gokhale, et al, *Gene Therapy* 4:1289-1299, 1997; Gao, and Huang, *Gene Therapy* 2:710-722, 1995, the disclosures of which are incorporated herein by reference in their entirety), by uptake of "naked DNA", and the like. In some instances, a method of delivery of the nucleic acids and/or DNA tolerizing vaccines may include or may be enhanced by electroporation, particle bombardment (i.e., biolistics), sonoporation, magnetofection, hydrodynamic delivery and the like. In some instances, a method of delivery of the nucleic acids and/or DNA tolerizing vaccines may include or may be enhanced by the use of one or more chemical methods to enhance delivery including but not limited to, e.g., the use of nucleic acid specifically modified to enhance delivery, lipoplexes, polymersomes, polyplexes, dendrimers, nanoparticles (e.g., inorganic nanoparticles), cell-penetrating peptides, cell-penetrating proteins (e.g., supercharged proteins), and the like. In some instances, the exact formulation, route of administration and dosage can be chosen empirically. Methods of nucleic acid and/or DNA vaccine delivery include but are not limited to, e.g., those described in U.S. Pat. Nos. 9,018,187, 8,877,729, 8,785,202, 8,759,499, 8,754,062, 8,747,903, 8,697,667, 8,591,862, 8,466,122, 8,338,584, 8,268,796, 8,242,089, 8,178,128, 7,922,709, 7,915,230, 7,829,657, 7,795,380, 7,795,017, 7,767,456, 7,655,467, 7,604,803, 7,534,424, 7,294,511, 7,015,040, the disclosures of which are incorporated herein by reference in their entirety.

Methods of interest for the delivery of nucleic acids and DNA vaccines, as described herein, include but are not limited to injection delivery, oral delivery, inhalation delivery, topical delivery (e.g., transdermal delivery, transmucosal delivery, etc.), and the like. Such delivery methods may or may not make use of methods for enhancing nucleic acid delivery, e.g., as described above, where appropriate. Of interest are injection delivery methods, including but not limited to needle and needleless injection methods. As such, in many instances, nucleic acids may be delivered in a suitable diluent by intramuscular injection and, in some instances, a course of therapy may include multiple intramuscular injections, e.g., according to a pre-determined treatment schedule. In some instances, methods of intramuscular injection of nucleic acids and DNA vaccines, as described herein, may include formulating the subject nucleic acid or DNA vaccine in phosphate buffered saline (PBS) containing 0.9 mM calcium ($Ca^{2+}$) as a sterile solution.

A pharmaceutical composition (e.g., a DNA vaccine composition) of the instant disclosure is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Kolliphor EL or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In some instances, methods as described herein my include methods for assaying for the effectiveness of a DNA tolerizing vaccine therapy. Methods of evaluating DNA tolerizing therapy effectiveness may include measuring the level of one or more biomarkers of NMO in a biological sample from the subject. In some instances, the level of an NMO biomarker may include the use of one or more specific binding agents of an aquaporin or an aquaporin antibody, e.g., for the detection and or measurement of an NMO biomarker. For example, in some instances, the level of one or more aquaporin antibodies (i.e., anti-APQ4-IgG, anti-APQ4-IgM, etc.) present in a biological sample from a subject may be measured through an assay involving binding of a detectable aquaporin antibody specific binding member to an aquaporin antibody of the sample.

In other instances, the level of an indirect biomarker, e.g., of aquaporin levels, of aquaporin antibody levels, of immune system activation, etc. may be measured or detected as a means of assessing a DNA tolerizing vaccine treatment as described herein. For example, in some instances the level of one or more immune system activation markers (e.g., one or more cytokines, IL-6, IL-17a, INF-gamma, etc.) may be measured in a biological sample from a subject as a means of determining the subject's response to treatment with a DNA tolerizing vaccine. In some instances, immunoglobulin levels may be assessed in a sample from a subject, including but not limited to, e.g., IgG levels, IgM levels, total immunoglobulin, etc., as a means of evaluating a subject's response to DNA tolerizing vaccine treatment. In some instances, the number, relative amounts, and/or activity of immune cells, e.g., collected from a biological sample from a subject, may be assessed as a means of determining a subject's response to DNA tolerizing vaccine treatment. Any convenient immune system evaluation assay may find use in assessing the immune system of a subject undergoing or having had treatment with a DNA tolerizing vaccine as described herein.

In some instances, a subject's response to therapy may be determined by measuring the response of one or more immune cell populations of the subject to the therapy. Immune cell populations that may be measured as a means of determining a subject's immune response may include but are not limited to, e.g., granulocytes and their progeny (e.g., basophils, eosinophils, and neutrophils), mast cells, monocytes and their progeny (e.g., macrophages, dendritic cells), natural killer cells, T cells (e.g., CD8+ T cells, CD4+ T cells (e.g., TH1 CD4+ T cells, TH2 CD4+ T cells, TH17 CD4+ T cells, and Treg CD4+ T cells), B cells, and the like. In some instances, a subject's response to treatment may be evaluated based on a subject's T cell response. In some instances, a subject's response to treatment may be evaluated based on a subject's B cell response. Methods of measuring a subject's immune system activity including response to therapy or autoimmune response include but are not limited to, e.g., T-cell proliferation assay, immunoblot assay, autoantibody detection, flow cytometric methods, etc. and those methods described in Seyfert-Margolis et al., *Diabetes.* 2006 55(9): 2588-2594; Bercovici et al., *Clin Vaccine Immunol.* 2000 7(6): 859-864; Gratama et al. *Cytometry A.* 2008 73(11): 971-974; the disclosures of which are incorporated herein by reference in their entirety. The ordinary artisan will readily recognize where a particular immune assay, e.g., an assay for a particular autoimmune disease, may be adapted for use in the methods as described herein, e.g., adaption of an existing autoimmune assay for evaluation of a treatment response as described herein and/or for the evaluation of NMO and/or a NMO spectrum disorder.

In some instances, assessments of a subject's immune system and/or immune response to a particular antigen may be performed prior to DNA tolerizing vaccine administration, e.g., to establish a baseline. In some instances, assessments of a subject's immune system and/or immune response to a particular antigen may be performed during therapy, e.g., at a pre-determined time point after the first administration and before the final administration, to assess a subject's response to DNA tolerizing vaccine therapy. In some instances, assessments of a subject's immune system and/or immune response to a particular antigen may be performed after therapy, e.g., at a pre-determined time point after administration of the final dose, to assess a subject's response to the course of DNA tolerizing vaccine treatment. In some instances, the results of such assessments may inform the therapeutic regimen and therapy may be adjusted, e.g., extended or terminated or modified (e.g., dose modification), based on the results of one or more of the assessments described herein.

Kits

Also provided are kits for use in the subject methods. The subject kits include any combination of components and compositions for performing the subject methods. In some embodiments, a kit can include the following: a DNA tolerizing vaccine, a vaccine delivery device, a suitable buffer and any combination thereof.

In some embodiments, a subject kit includes lyophilized DNA tolerizing vaccine and a suitable diluent for resuspending the lyophilized DNA tolerizing vaccine before use where the DNA tolerizing vaccine and the diluent are present in separate containers. In some instances, a subject kit may include one or more pre-formulated doses of DNA tolerizing vaccine in "ready-to-use" format. In instances where a dosing regimen is desired that includes multiple administrations of one or more DNA tolerizing vaccines, a subject kit may include two or more doses of DNA tolerizing vaccine, in a pre-formulated or an unformulated configuration, and may, optionally, include instructions (e.g., instructions as to when each dose should be administered, instruction for preparing unformulated doses, instructions for dose delivery, etc.). In some instances, a subject kit may include one or more testing reagents or testing devices or combinations thereof for assaying a subject's need for therapy (e.g., before or after therapy), assaying the effectiveness of therapy (e.g., during or after therapy), etc.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (pl); seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Example 1

Figure 2:
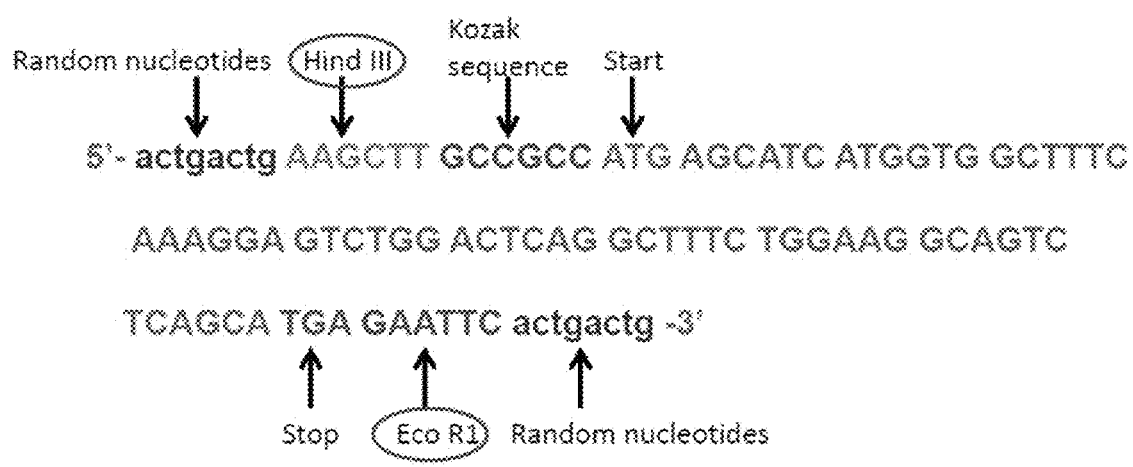
FIG. 2 depicts the antigen portion of the pBHT1-murine AQP4 p21-40 construct. The construct was constructed by digesting double stranded AQP4 p21-40 oligonucleotide and pBHT1 with HindIII and EcoRI restriction enzymes, removing the 5' phosphates from pBHT1 and performing a ligation reaction. The ligated vector was then transformed into bacteria and the transformed bacteria were plated (SEQ ID NO:1).

A tolerizing DNA vaccine minigene was developed using AQP4 peptide 21-40 inserted into a modified pBHT1 expression vector (FIG. 1). The modified pBHT1 expression vector has been modified to reduce the CpG sequences in the noncoding backbone. Modified pBHT1 and AQP4p21-40 encoding oligos were digested with HindIII and EcoRI (FIG. 2), 5' phosphates from pBHT1 were removed, and the resultant polynucleotides were ligated. Newly ligated plasmids were transformed, plated, and screened. Presence of the AQP4p21-40 insert (100 bp) was verified by restriction enzyme digest of the newly ligated plasmid (FIG. 3) and DNA sequencing/BLAST (FIG. 4).

The 21-40 AQP4 peptide sequence is the dominant T cell epitope in both SJLJ and C57BL6 mice. In comparison, the dominate T cell epitope in humans is AQP4 peptide 61-80 (see, e.g., Nelson et al. (2010) PLOS one, 5(11):e15050 and Varrin-Doyer et al. (2012) Ann Neurol, 72(1):53-64, the disclosures of which are incorporated herein by reference in their entirety).

Figure 5:
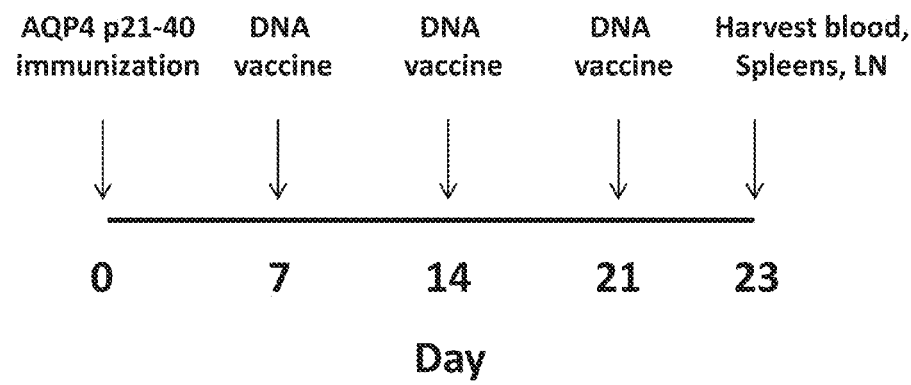
FIG. 5 depicts a schematic of NMO mouse model DNA vaccination experiment #1. Arrows along the timeline represent when each action of the experiment was performed. 10 C57BL6 mice were used in 3 groups (2 immunized mice that did not receive treatment, 4 immunized mice that received treatment with empty DNA vaccine vector and 4 immunized mice that received treatment with the AQP4p21-40 DNA vaccine vector).
Figure 6:
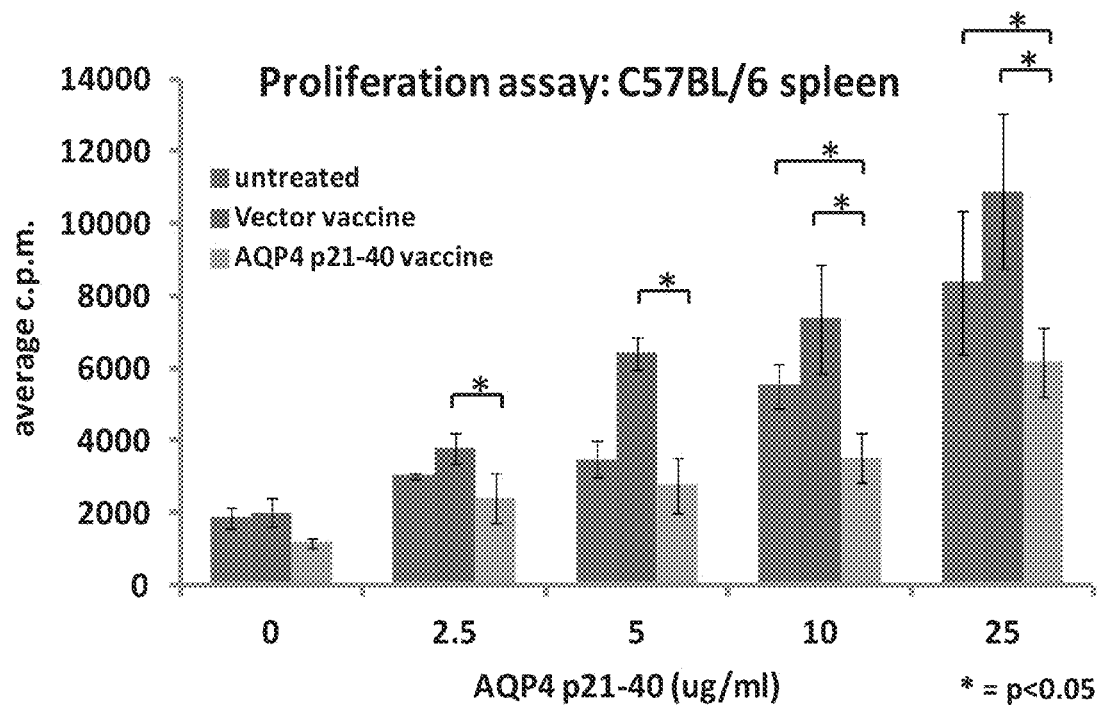
FIG. 6 depicts that the AQP4 p21-40 DNA vaccination is effective in suppressing AQP4 p21-40 specific T cell proliferation. Proliferation assay was performed using the spleens of untreated mice, mice treated with empty vector, and mice treated with AQP4p21-40 DNA vaccine and T cell stimulation was performed at various concentrations of antigen (x-axis). Statistically significant differences at $p<0.05$ are indicated (*).
Figure 7:
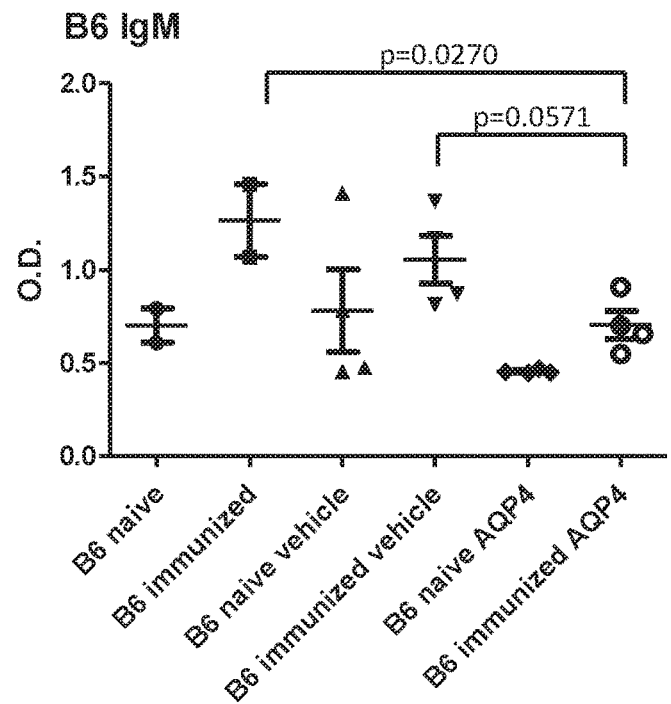
FIG. 7 depicts that AQP4 p21-40 IgM antibodies decreased following DNA vaccination in C57BL/6 mice. B6 IgM levels were measured in mice that were not immunized and did not receive treatment (B6 naïve), mice that were immunized but did not receive treatment (B6 immunized), mice that were not immunized and treated with empty vehicle (B6 naïve vehicle), mice that were immunized and treated with empty vehicle (B6 immunized vehicle), mice that were not immunized and treated with AQP4 DNA vaccine (B6 naïve AQP4) and mice that were immunized and treated with AQP4 DNA vaccine (B6 immunized AQP4).
Figure 8:
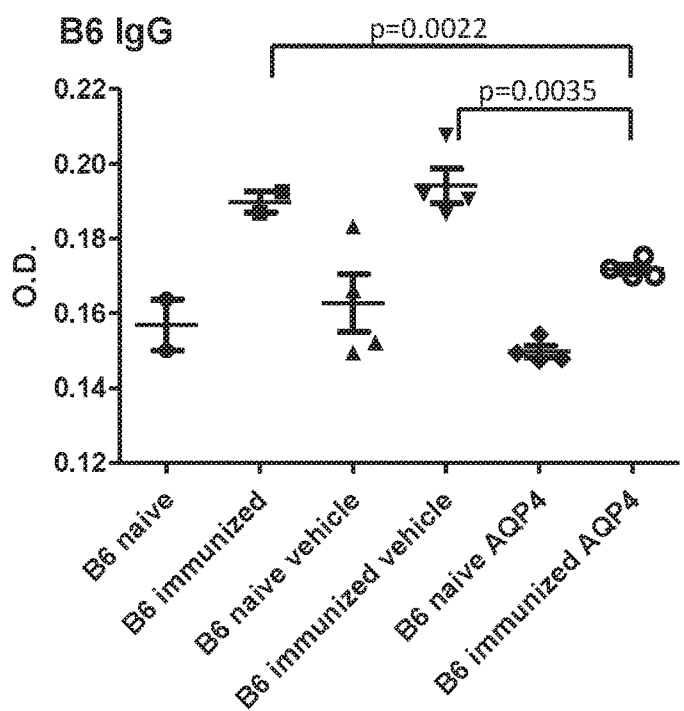
FIG. 8 depicts that AQP4 p21-40 IgG antibodies decreased following DNA Vaccination in C57BL/6 mice. B6 IgG levels were measured in mice that were not immunized and did not receive treatment (B6 naïve), mice that were immunized but did not receive treatment (B6 immunized), mice that were not immunized and treated with empty vehicle (B6 naïve vehicle), mice that were immunized and treated with empty vehicle (B6 immunized vehicle), mice that were not immunized and treated with AQP4 DNA vaccine (B6 naïve AQP4) and mice that were immunized and treated with AQP4 DNA vaccine (B6 immunized AQP4).
Figure 9:
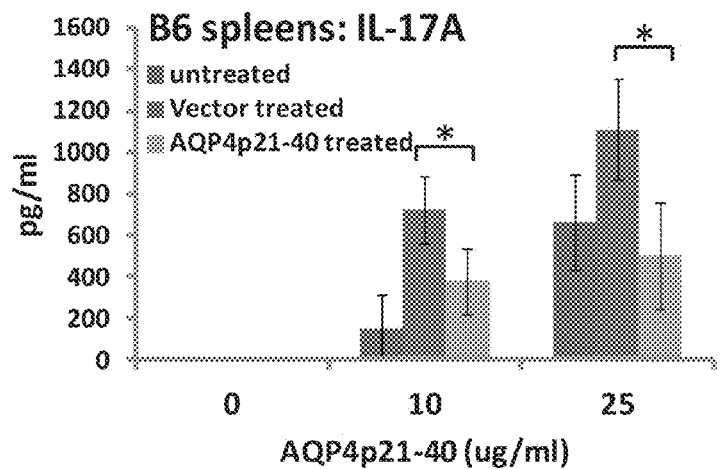
FIG. 9 depicts that AQP4 p21-40 DNA vaccination is effective in suppressing IL-17A. IL-17A production was measured at various concentrations of antigen (x-axis) in untreated mice, mice treated with empty vector, and mice treated with AQP4p21-40 DNA vaccine. Statistically significant differences are indicated (*).
Figure 10:
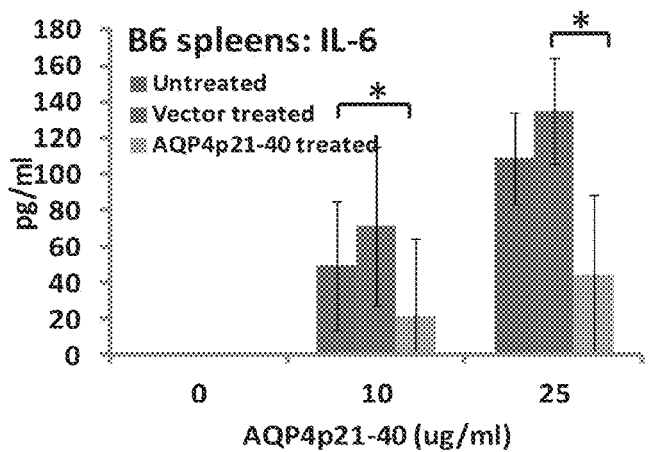
FIG. 10 depicts that AQP4 p21-40 DNA vaccination is effective in suppressing IL-6. IL-6 production was measured at various concentrations of antigen (x-axis) in untreated mice, mice treated with empty vector, and mice treated with AQP4p21-40 DNA vaccine. Statistically significant differences are indicated (*).
Figure 11:
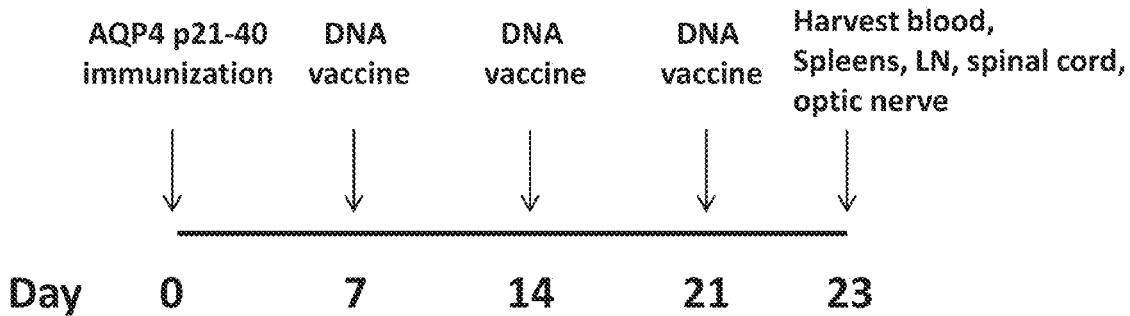
FIG. 11 depicts a schematic of NMO mouse model DNA vaccination experiment #2. Arrows along the timeline represent when each action of the experiment was performed. 15 C57BL6 mice were used in 3 groups (5 immunized mice that did not receive treatment, 5 immunized mice that received treatment with empty DNA vaccine vector and 5 immunized mice that received treatment with the AQP4p21-40 DNA vaccine vector).
Figure 12:
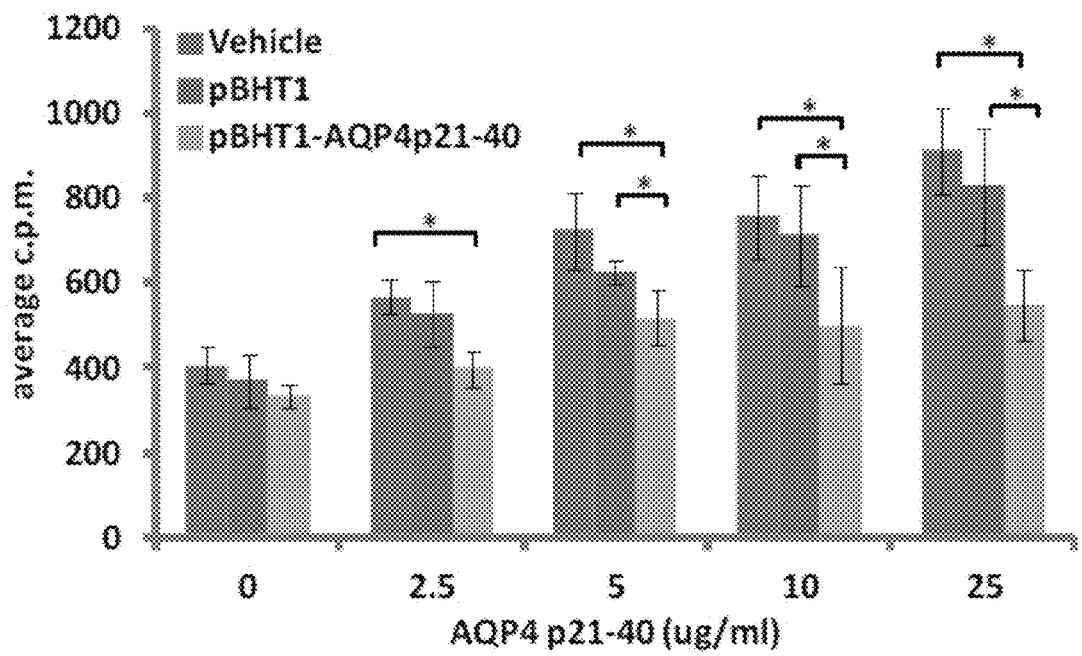
FIG. 12 depicts that AQP4 p21-40 DNA vaccination is effective in suppressing AQP4 p21-40 specific T cell proliferation. Proliferation assay was performed using untreated mice, mice treated with empty pBHT1 vector, and mice treated with pBHT1-AQP4p21-40 DNA vaccine and T cell stimulation was performed at various concentrations of antigen (x-axis). Statistically significant differences at are indicated (*).
Figure 13:
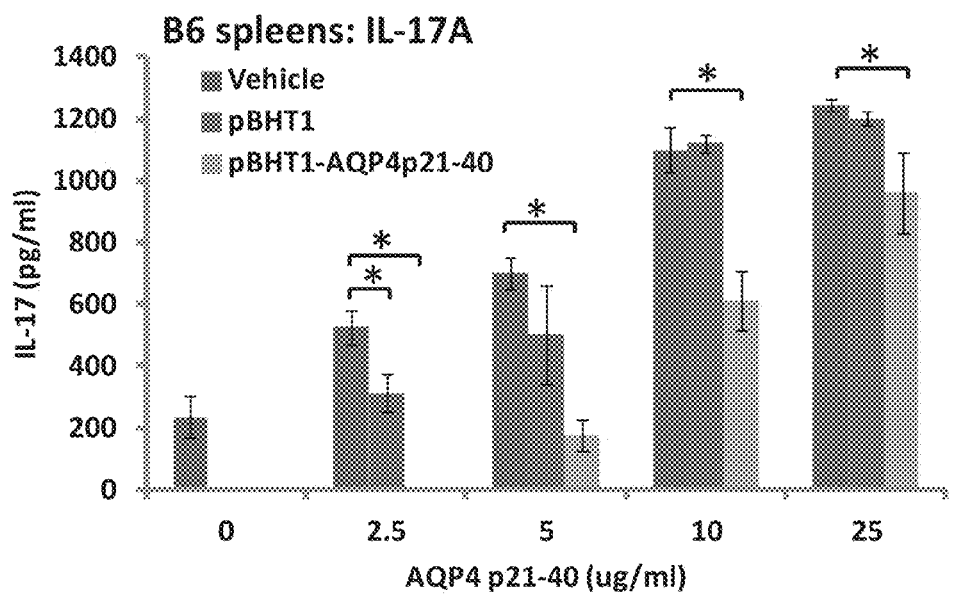
FIG. 13 depicts that AQP4 p21-40 DNA vaccination is effective in suppressing IL-17A. IL-17A production was measured at various concentrations of antigen (x-axis) in mice that received only delivery vehicle (vehicle), mice treated with empty vector (pBHT1), and mice treated with p-BHT1-AQP4p21-40 DNA vaccine (p-BHT1-AQP4p21-40 DNA). Statistically significant differences are indicated (*).
Figure 14:
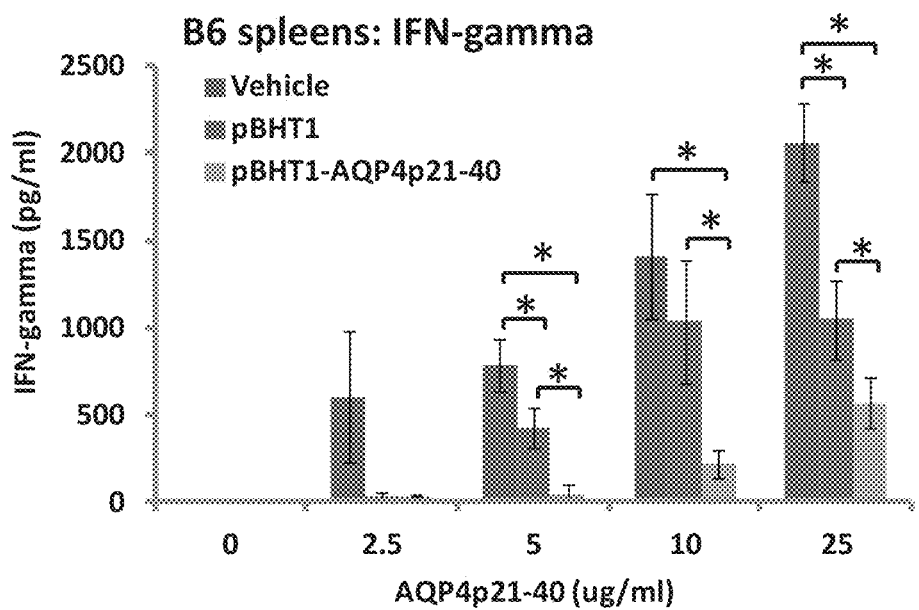
FIG. 14 depicts that AQP4 p21-40 DNA vaccination is effective in suppressing IFN-gamma. IFN-gamma production was measured at various concentrations of antigen (x-axis) in mice that received only delivery vehicle (vehicle), mice treated with empty vector (pBHT1), and mice treated with p-BHT1-AQP4p21-40 DNA vaccine (p-BHT1-AQP4p21-40 DNA). Statistically significant differences are indicated (*).
Figure 15:
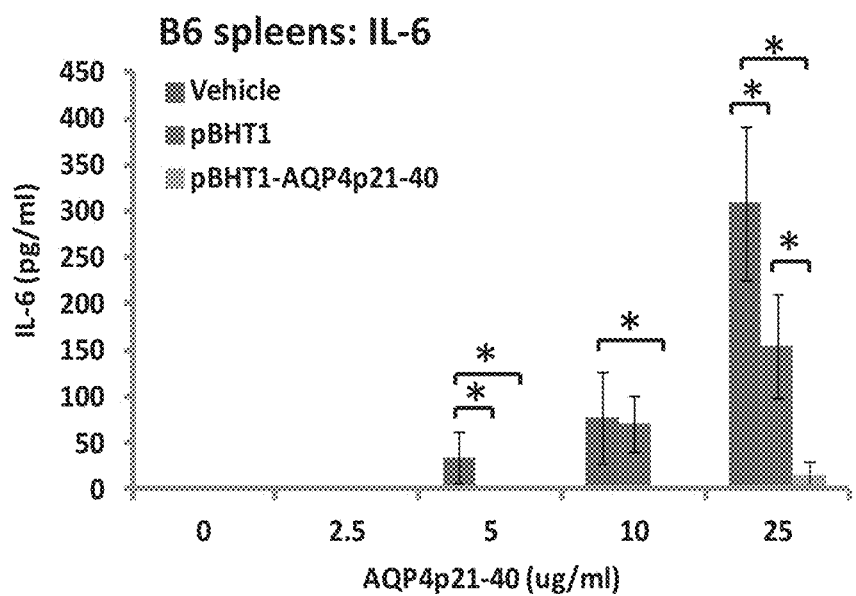
FIG. 15 depicts that AQP4 p21-40 DNA vaccination is effective in suppressing IL-6. IL-6 production was measured at various concentrations of antigen (x-axis) in mice that received only delivery vehicle (vehicle), mice treated with empty vector (pBHT1), and mice treated with p-BHT1-AQP4p21-40 DNA vaccine (p-BHT1-AQP4p21-40 DNA). Statistically significant differences are indicated (*).
Figure 16:
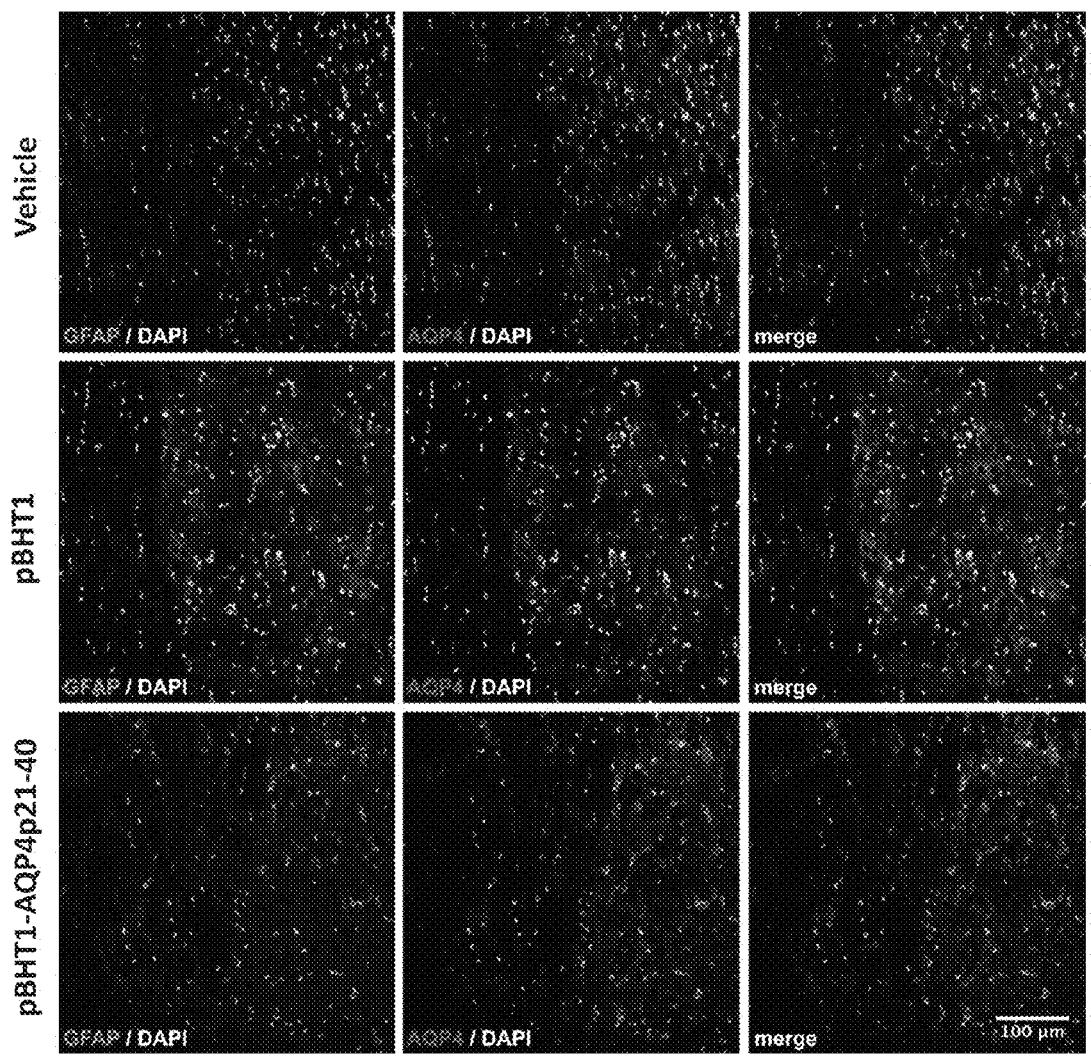
FIG. 16 depicts that AQP4 p21-40 DNA vaccination maintains AQP4 expression on astrocytes in AQP4 p21-40-immunized spinal cord. Astrocytes from mice that received only delivery vehicle (vehicle, top row), mice treated with empty vector (pBHT1, middle row), and mice treated with p-BHT1-AQP4p21-40 DNA vaccine (p-BHT1-AQP4p21-40 DNA, bottom row) were stained for GFAP (left column) and AQP4 (middle column) and DNA (DAPI) and imaged (merged images (right column) showing both GFAP and AQP4 staining are also provided). Staining and imaging displayed that AQP4 expression is maintained in astrocytes from AQP4p21-40 immunized spinal cord.

In two separate trials, C57BL6 mice were immunized with AQP4 peptide 21-40 in complete Freund's adjuvant. On days 7, 14, and 21, the mice were given intramuscular injections of vehicle (1×PBS, with calcium and magnesium), empty pBHT1 vector, or pBHT1-AQP4p21-40 tolerizing DNA vaccine (see FIG. 5 and FIG. 11 for experimental timelines). On day 23, spleens and serum or spleens, serum, spinal cord and optic nerve were harvested from the mice (see FIG. 5 and FIG. 11). 72 hour T cell proliferation assays in the presence of AQP4 p21-40 showed a statistically significant reduction in T cell proliferation from the mice treated with AQP4p21-40 tolerizing DNA vaccine compared to the two control groups (FIG. 6 and FIG. 12). ELISAs performed on the cellular supernatants showed a decrease in IL-6, IL-17, and IFN-gamma production in the AQP4p21-40 tolerizing DNA vaccine treated mice as compared to the two control groups (FIG. 9, FIG. 10, FIG. 13, FIG. 14 and FIG. 15). ELISA analysis of the serum indicated that AQP4p21-40 specific IgM and IgG antibodies were also significantly reduced in the AQP4p21-40 tolerizing DNA vaccine treated mice as compared to the two control groups (FIG. 7 and FIG. 8). Furthermore, Glial fibrillary acidic protein (GFAP) staining (a marker for astrocytes) and AQP4 staining in astrocytes from AQP4 p21-40-immunized spinal cord indicates that AQP4 p21-40 DNA vaccination results in the maintenance of astrocyte AQP4 expression (FIG. 16).

These experiments conclusively show that pBHT1-AQP4p21-40 tolerizing DNA vaccine is effective in suppressing both T cell and B cell responses to AQP4 p21-40 in mice.

Example 2

Human specific AQP4 tolerizing DNA vaccines are generated, including AQP4p61-80 minigene DNA vaccine and full-length AQP4 cDNA vaccine. Human specific AQP sequences, including AQP4p61-80 and full-length AQP4 cDNA, are cloned into modified pBHT1 expression vector.

Mice, optionally humanized mice (e.g., humanized-NSG mice (e.g., CD34 humanized mice, BLT humanized mice, PBMC humanized mice, and the like) available from The Jackson Laboratory (Bar Harbor, Me.)), are immunized with either human AQP4 peptide or full-length human AQP4 or a combination thereof. Following immunization, mice are given intramuscular injections of vehicle, empty vector, or one or more human specific AQP4 tolerizing DNA vaccines according to a predetermined injection schedule. At a predetermined time-point spleens and serum are harvested from the mice. Assays are performed to evaluate immune system response in the mice, e.g. T cell and B cell responses, IL-6, IL-7 and IFN-gamma production, and the like. The results of the assays for the experimental and control groups are compared to evaluate the effect of human specific AQP4 tolerizing DNA vaccines on immune response in the AQP4 immunized mice.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method for reducing adverse B cell and T cell responses in a subject with Neuromyelitis optica (NMO) the method comprising:
   administering by intramuscular injection to the subject an effective amount of an APQ4 DNA tolerizing vaccine comprising:
   a) a nucleic acid sequence encoding an aquaporin polypeptide comprising amino acids 61-80 of human APQ4;
   b) a promoter sequence operably linked the nucleic acid sequence; and
   c) a DNA backbone, linked to the promoter sequence and the nucleic acid sequence, comprising 4 or fewer immunostimulatory CpG motifs wherein the aquaporin polypeptide is modified and encodes a non-naturally occurring aquaporin polypeptide.

2. The method of claim 1, wherein aquaporin specific IgG and IgM antibodies are reduced in serum of the subject following administration of the APQ4 DNA tolerizing vaccine.

3. The method of claim 1, wherein astrocyte aquaporin expression is maintained.

4. A method for reducing adverse B cell and T cell responses in a subject with Neuromyelitis optica (NMO), the method comprising:
   administering by intramuscular injection to the subject an effective amount of an APQ4 DNA tolerizing vaccine comprising:
   a) a nucleic acid sequence encoding an aquaporin polypeptide consisting of amino acids 61-80 of human APQ4;
   b) a promoter sequence operably linked the nucleic acid sequence; and
   c) a DNA backbone, linked to the promoter sequence and the nucleic acid sequence, in which one or more CpG dinucleotides of the formula 5'-purine-pyrimidine-C-G-pyrimidine-pyrimidine-3' are mutated by substituting cytosine of the CpG dinucleotide with a non-cytosine nucleotide to comprise 4 or fewer immunostimulatory CpG motifs.

5. The method of claim 4, wherein the DNA backbone comprises SEQ ID NO:7.

6. The method of claim 4, wherein aquaporin specific IgG and IgM antibodies are reduced in serum of the subject following administration of the APQ4 DNA tolerizing vaccine.

7. The method of claim 4, wherein astrocyte aquaporin expression is maintained.

* * * * *

SEQUENCE LISTING

<160> NUMBER OF SEQ ID NOS: 7

<210> SEQ ID NO 1
<211> LENGTH: 100
<212> TYPE: DNA
<213> ORGANISM: Artificial sequence
<220> FEATURE:
<223> OTHER INFORMATION: synthetic polynucleotide sequence

<400> SEQUENCE: 1

```
actgactgaa gcttgccgcc atgagcatca tggtggcttt caaaggagtc tggactcagg      60
ctttctggaa ggcagtctca gcatgagaat tcactgactg                           100
```

<210> SEQ ID NO 2
<211> LENGTH: 72
<212> TYPE: DNA
<213> ORGANISM: Artificial sequence
<220> FEATURE:
<223> OTHER INFORMATION: synthetic polynucleotide sequence

<400> SEQUENCE: 2

```
gagcatcatg gtggctttca aaggagtctg gactcaggct ttctggaagg cagtctcagc      60
atgagaattc tg                                                          72
```

<210> SEQ ID NO 3
<211> LENGTH: 323
<212> TYPE: PRT
<213> ORGANISM: Homo sapiens

<400> SEQUENCE: 3

```
Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
        115                 120                 125

Gly Ala Gly Ile Leu Tyr Leu Val Thr Pro Pro Ser Val Val Gly Gly
    130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
        195                 200                 205

Gly Ala Ser Met Asn Pro Ala Arg Ser Phe Gly Pro Ala Val Ile Met
    210                 215                 220
```

```
Gly Asn Trp Glu Asn His Trp Ile Tyr Trp Val Gly Pro Ile Ile Gly
225                 230                 235                 240

Ala Val Leu Ala Gly Leu Tyr Glu Tyr Val Phe Cys Pro Asp Val
            245                 250                 255

Glu Phe Lys Arg Arg Phe Lys Glu Ala Phe Ser Lys Ala Ala Gln Gln
            260                 265                 270

Thr Lys Gly Ser Tyr Met Glu Val Glu Asp Asn Arg Ser Gln Val Glu
            275                 280                 285

Thr Asp Asp Leu Ile Leu Lys Pro Gly Val Val His Val Ile Asp Val
            290                 295                 300

Asp Arg Gly Glu Glu Lys Lys Gly Lys Asp Gln Ser Gly Glu Val Leu
305                 310                 315                 320

Ser Ser Val

<210> SEQ ID NO 4
<211> LENGTH: 323
<212> TYPE: PRT
<213> ORGANISM: Mus musculus

<400> SEQUENCE: 4

Met Ser Asp Gly Ala Ala Arg Arg Trp Gly Lys Cys Gly His Ser
1               5                   10                  15

Cys Ser Arg Glu Ser Ile Met Val Ala Phe Lys Gly Val Trp Thr Gln
                20                  25                  30

Ala Phe Trp Lys Ala Val Ser Ala Glu Phe Leu Ala Thr Leu Ile Phe
            35                  40                  45

Val Leu Leu Gly Val Gly Ser Thr Ile Asn Trp Gly Gly Ser Glu Asn
50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ile Ala Gln Cys Leu Gly Ala Ile Ile
            115                 120                 125

Gly Ala Gly Ile Leu Tyr Leu Val Thr Pro Pro Ser Val Val Gly Gly
            130                 135                 140

Leu Gly Val Thr Thr Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
            195                 200                 205

Gly Ala Ser Met Asn Pro Ala Arg Ser Phe Gly Pro Ala Val Ile Met
            210                 215                 220

Gly Asn Trp Ala Asn His Trp Ile Tyr Trp Val Gly Pro Ile Met Gly
225                 230                 235                 240

Ala Val Leu Ala Gly Ala Leu Tyr Glu Tyr Val Phe Cys Pro Asp Val
                245                 250                 255

Glu Leu Lys Arg Arg Leu Lys Glu Ala Phe Ser Lys Ala Ala Gln Gln
            260                 265                 270
```

Thr Lys Gly Ser Tyr Met Glu Val Glu Asp Asn Arg Ser Gln Val Glu
       275                 280                 285

Thr Glu Asp Leu Ile Leu Lys Pro Gly Val Val His Val Ile Asp Ile
       290                 295                 300

Asp Arg Gly Glu Glu Lys Lys Gly Lys Asp Ser Ser Gly Glu Val Leu
305                 310                 315                 320

Ser Ser Val

<210> SEQ ID NO 5
<211> LENGTH: 972
<212> TYPE: DNA
<213> ORGANISM: Homo sapiens

<400> SEQUENCE: 5

```
atgagtgaca gacccacagc aaggcggtgg ggtaagtgtg gacctttgtg taccagagag    60
aacatcatgg tggctttcaa aggggtctgg actcaagctt tctggaaagc agtcacagcg   120
gaatttctgg ccatgcttat ttttgttctc ctcagcctgg gatccaccat caactggggt   180
ggaacagaaa agcctttacc ggtcgacatg gttctcatct ccctttgctt tggactcagc   240
attgcaacca tggtgcagtg cttggccat atcagcggtg ccacatcaa ccctgcagtg    300
actgtggcca tggtgtgcac caggaagatc agcatcgcca gtctgtctt ctacatcgca   360
gcccagtgcc tggggccat cattggagca ggaatcctct atctggtcac acctcccagt   420
gtggtgggag gcctgggagt caccatggtt catggaaatc ttaccgctgg tcatggtctc   480
ctggttgagt tgataatcac atttcaattg gtgtttacta tctttgccag ctgtgattcc   540
aaacggactg atgtcactgg ctcaatagct ttagcaattg tttgctgt tgcaattgga   600
cattatttg caatcaatta tactggtgcc agcatgaatc ccgcccgatc ctttggacct   660
gcagttatca tgggaaattg gaaaaccat tggatatatt gggttgggcc catcatagga   720
gctgtcctcg ctggtggcct ttatgagtat gtcttctgtc cagatgttga attcaaacgt   780
cgttttaaag aagccttcag caaagctgcc cagcaaacaa aaggaagcta catggaggtg   840
gaggacaaca ggagtcaggt agagacggat gacctgattc taaaacctgg agtggtgcat   900
gtgattgacg ttgaccgggg agaggagaag aaggggaaag accaatctgg agaggtattg   960
tcttcagtat ga                                                      972
```

<210> SEQ ID NO 6
<211> LENGTH: 972
<212> TYPE: DNA
<213> ORGANISM: Mus musculus

<400> SEQUENCE: 6

```
atgagtgaca gagctgcggc aaggcggtgg ggtaagtgtg gacattcctg cagtagagag    60
agcatcatgg tggctttcaa aggagtctgg actcaggctt tctggaaggc agtctcagca   120
gaatttctgg ccacgcttat ctttgttttg ctcggtgtgg gatccaccat aaactggggt   180
ggctcagaaa accccttacc tgtggacatg gtcctcatct ccctttgctt tggactcagc   240
attgctacca tggtgcagtg cttggccac atcagtggtg ccacatcaa tcccgctgtg    300
actgtagcca tggtgtgcac acgaaagatc agcatcgcta agtccgtctt ctacatcatt   360
gcacagtgcc tggggccat cattggagcc ggcatcctct acctggtcac acctcccagt   420
gtggttggag gattgggagt caccacggtt catggaaacc tcaccgctgg ccatgggctc   480
ctggtggagt taataatcac tttccagttg gtgttcacta tttttgccag ctgtgattcc   540
```

```
aaacgaactg atgttactgg ttcaatagct ttagcaattg gattttccgt tgcaattgga      600
catttgtttg caatcaatta tactggagcc agcatgaatc cagctcgatc ttttggaccc      660
gcagttatca tgggaaactg gcaaaccac tggatatatt gggttggacc aatcatgggc       720
gctgtgctgg caggtgccct ttatgagtat gtcttctgtc ctgatgtgga gctcaaacgt      780
cgccttaagg aagccttcag caaagccgcg cagcagacaa agggagcta catggaggtg       840 gaggacaacc ggagccaagt ggagacggaa gacttgatcc tgaagcccgg agtggtgcat      900
gtgattgaca ttgaccgtgg agaagagaag aaggggaaag actcttcggg agaggtattg      960
tcttccgtat ga                                                         972

<210> SEQ ID NO 7
<211> LENGTH: 2999
<212> TYPE: DNA
<213> ORGANISM: Artificial sequence
<220> FEATURE:
<223> OTHER INFORMATION: synthetic polynucleotide sequence

<400> SEQUENCE: 7
gactcttcgc gatgtacggg ccagatatac gcgttgacat tgattattga ctagttatta       60
atagtaatca attacggggt cattagttca tagcccatat atggagttcc gcgttacata      120
acttacggta aatggcccgc ctggctgacc gcccaacgac ccccgcccat tgacgtcaat      180
aatgacgtat gttcccatag taacgccaat agggactttc cattgacgtc aatgggtgga      240
ctatttacgg taaactgccc acttggcagt acatcaagtg tatcatatgc caagtacgcc      300
ccctattgac gtcaatgacg gtaaatggcc cgcctggcat tatgcccagt acatgacctt      360
atgggacttt cctacttggc agtacatcta cgtattagtc atcgctatta ccatggtgat      420
gcggttttgg cagtacatca atgggcgtgg atagcggttt gactcacggg gatttccaag      480
tctccacccc attgacgtca atgggagttt gttttggcac caaaatcaac gggactttcc      540
aaaatgtcgt aacaactccg ccccattgac gcaaatgggc ggtaggcgtg tacggtggga      600
ggtctatata agcagagctc tctggctaac tagagaaccc actgcttact ggcttatcga      660
aattaatacg actcactata gggagaccca agctggctag cgtttaaact taagcttggt      720
accgagctcg gatccactag tccagtgtgg tggaattctg cagatatcca gcacagtggc      780
ggcggctcga gtctagaggg cccgtttaaa cccgctgatc agcctcgact gtgccttcta      840
gttgccagcc atctgttgtt tgcccctccc ccgtgccttc cttgaccctg gaaggtgcca      900
ctcccactgt cctttcctaa taaaatgagg aaattgcatc gcattgtctg agtaggtgtc      960
attctattct ggggggtggg gtggggcagg acagcaaggg ggaggattgg gaagacaata     1020
gcaggcatgc tggggatgcg gtgggctcta tggcttctac tgggcggttt tatgacagc      1080 aagcgaaccg gaattgccag ctggggcgcc ctctggtaag gttgggaagc cctgcaaagt     1140
aaactggatg gctttctcgc cggccaagga tctgatgcgc aggggatcaa gctctgatca     1200
agagacagga tgaggatggt ttcgcatgat tgaacaagat ggattgcacg caggttctcc     1260
ggcagcttgg gtggagaggc tattcggcta tgactgggca caacagacaa tcggctgctc     1320
tgatgccgcc gtgttcaggc tgtcagcgca ggggcgcccg gttcttttttg tcaagaccga     1380 cctgtccggt gccctgaatg aactgcaaga cgaggcagcg cggctatcgt ggctggccac     1440
gacgggcgtt ccttgcgcag ctgtgctcga cgttgtcact gaagcgggaa gggactggct     1500
gctattgggc gaagtgccgg ggcaggatct cctgtcatct caccttgctc ctgccgagaa     1560
```

```
agtatccatc atggctgatg caatgcggcg gctgcatacg cttgatccgg ctacctgccc    1620
attcgaccac caagcgaaac atcgcatcga gcgagcacgt actcggatgg aagccggtct    1680
tgtcgatcag gatgatctgg acgaagagca tcaggggctc gcgccagccg aactgttcgc    1740
caggctcaag gcgagcatgc ccgacggcga ggatctcgtc gtgacccatg gcgatgcctg    1800
cttgccgaat atcatggtgg aaaatggcag gttttctgga ttcatcgact gtggccggct    1860
gggtgtggcg gacaggtatc aggacatagc gttggctacc cgtgatattg ctgaagagct    1920
tggcggcgaa tgggctgaca ggttcctcgt gctttacggt attgcggctc ccgattcgca    1980
gcgcattgcc ttctataggc ttcttgacga gttcttctga attattaacg cttacaattt    2040
cctgatgcgg tattttctcc ttacgcatct gtgcggtatt tcacaccgca tacaggtggc    2100
acttttcggg gaaatgtgcg cggaacccct atttgtttat ttttctaaat acattcaaat    2160
atgtatccgc tcatgagaca ataaccctga taaatgcttc aataatagca cgtgctaaaa    2220 cttcatttt  aatttaaaag gatctaggtg aagatccttt ttgataatct catgaccaaa    2280
atcccttaac gtgagttttc gttccactga gcgtcagacc ccgtagaaaa gatcaaagga    2340
tcttcttgag atcctttttt tctgcgcgta atctgctgct tgcaaacaaa aaaaccaccg    2400
ctaccagcgg tggtttgttt gccggatcaa gagctaccaa ctcttttcc  gaaggtaact    2460 ggcttcagca gagcgcagat accaaatact gtccttctag tgtagccgta gttaggccac    2520
cacttcaaga actctgtagc accgcctaca tacctcgctc tgctaatcct gttaccagtg    2580
gctgctgcca gtggcgataa gtcgtgtctt accgggttgg actcaagacg atagttaccg    2640
gataaggcgc agcggtcggg ctgaacgggg gttcgtgca  cacagcccag cttggagcga    2700
acgacctaca ccgaactgag atacctacag cgtgagctat gagaaagcgc cacgcttccc    2760
gaagggagaa aggcggacag gtatccggta agcggcaggg tcggaacagg agagcgcacg    2820
agggagcttc caggggggaaa cgcctggtat ctttatagtc ctgtcgggtt tcgccacctc    2880
tgacttgagc gtcgattttt gtgatgctcg tcaggggggc ggagcctatg gaaaaacgcc    2940
agcaacgcgg cctttttacg gttcctgggc ttttgctggc cttttgctca catgttctt    2999
```